United States Patent

Minagawa et al.

[11] 4,312,804
[45] Jan. 26, 1982

[54] 2,2,6,6-TETRAALKYL-4-PIPERIDYL ALCOHOL ESTERS OF TETRADECYLENE POLYCARBOXYLIC ACIDS AS LIGHT STABILIZERS FOR SYNTHETIC POLYMERS

[75] Inventors: Motonobu Minagawa, Koshigaya; Naohiro Kubota, Ageo; Toshihiro Shibata, Omiya, all of Japan

[73] Assignee: Argus Chemical Corporation, Brooklyn, N.Y.

[21] Appl. No.: 171,633

[22] Filed: Jul. 23, 1980

[30] Foreign Application Priority Data

Jul. 23, 1979 [JP] Japan .................. 54-92620

[51] Int. Cl.³ ............... C07D 401/14; C07D 491/113; C08K 5/34; C08K 5/35
[52] U.S. Cl. ..................... 260/45.8 NZ; 260/45.8 N; 546/17; 546/188
[58] Field of Search .................. 260/45.8 N, 45.8 NZ; 546/17, 188

[56] References Cited

U.S. PATENT DOCUMENTS 4,016,168  4/1977  Murayama et al. ........ 260/45.8 NZ
4,136,081  1/1979  Minagawa et al. ......... 260/45.8 NP
4,141,883  2/1979  Soma et al. ................. 260/45.8 NP Primary Examiner—John Kight, III
Assistant Examiner—R. A. White

[57] ABSTRACT

2,2,6,6-Tetraalkyl-4-piperidyl alcohol esters of tetradecylene polycarboxylic acids are provided, useful as light stabilizers for organic polymeric materials, and having the general formula:

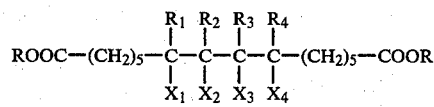

in which
R is selected from the group consisting of

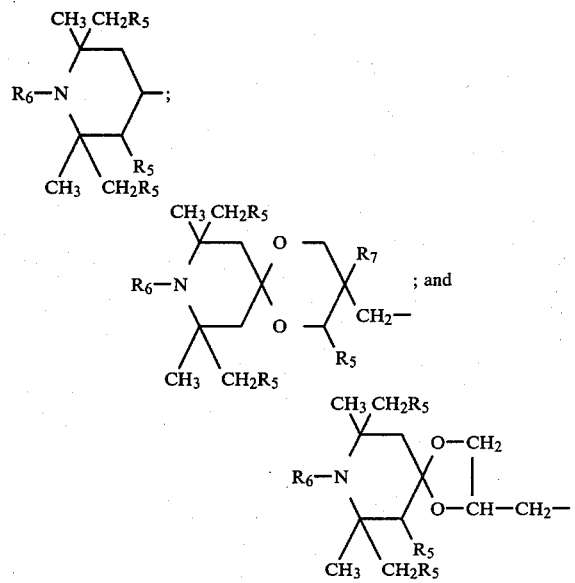

wherein:
$R_5$ and $R_6$ are each hydrogen or lower alkyl or hydroxyalkyl having from one to about six carbon atoms;
$R_7$ is lower alkyl having from one to about six carbon atoms;
$R_1$, $R_2$, $R_3$ and $R_4$ are selected from the group consisting of hydrogen and methyl;
$X_1$ and $X_3$ are selected from the group consisting of hydrogen and COOR;
$X_2$ and $X_4$ are selected from the group consisting of COOR and

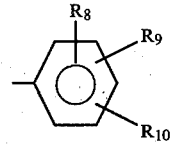

30 wherein
$R_8$, $R_9$ and $R_{10}$ are selected from the group consisting of hydrogen, hydroxy, alkyl, and alkoxy having from one to about eighteen carbon atoms.

28 Claims, No Drawings

2,2,6,6-TETRAALKYL-4-PIPERIDYL ALCOHOL ESTERS OF TETRADECYLENE POLYCARBOXYLIC ACIDS AS LIGHT STABILIZERS FOR SYNTHETIC POLYMERS

Hindered 2,2,6,6-tetraalkyl-4-carboxylic acid ester piperidine compounds having been proposed by Murayama et al U.S. Pat. No. 3,640,928, patented Feb. 8, 1972 as light and heat stabilizers for synthetic polymers, such as polyolefins, polyvinyl chloride, polyvinylidene chloride, polyurethanes, and polyamides. These compounds have the general formula:

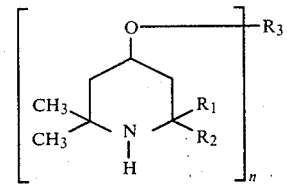

or a salt thereof.

In the above formula:

$R_1$ and $R_2$ which may be the same or different, each are an alkyl group such as methyl, ethyl, isopropyl or dodecyl, or they form, together with the carbon atom to which they are attached, a saturated alicyclic group such as:

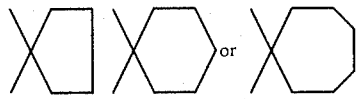

or a group of the formula

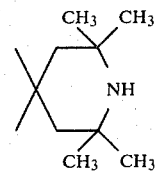

n is an integer of 1 to 3 inclusive; and $R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al and others of compounds including a 2,2,6,6-tetrasubstituted-4-piperidyl group attached to a base molecule of varying structures.

Murayama et al U.S. Pat. No. 3,790,525, patented Feb. 5, 1974, provides synthetic polymer compositions stabilized against photo- and thermal-deterioration incorporating in the composition an effective amount of a 4-piperidone ketal having the formulae:

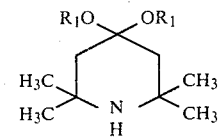

and

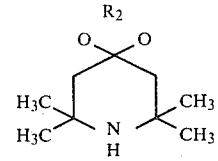

wherein $R_1$ represents an alkyl group of one to eight carbon atoms and $R_2$ represents an alkylene group of two or three carbon atoms or o-phenylene group.

Murayama et al U.S. Pat. No. 3,898,303 patented Aug. 5, 1975 propose piperidino-spiro-hydantoin derivatives having the formula:

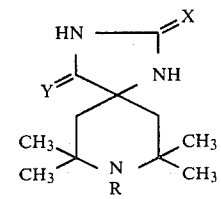

wherein:

R represents an alkyl group, an alkenyl group, an alkenoyl group which may be substituted with an aryl group, a hydroxyalkyl group, an alkoxy-alkyl group, an alkoxycarbonylalkyl group, an acyloxyalkyl group, a cyanoalkyl group or nitroso group, and X and Y individually represent oxygen atom or sulfur atom.

Murayama et al in U.S. Pat. No. 3,899,464 patented Aug. 12, 1975 discloses a variation of the piperidino spiro compounds having the formula:

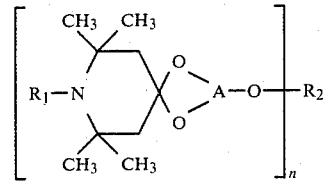

wherein:

$R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4;

when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, a N-substituted carbamoyl group, a N-substituted thiocarbamoyl group, a monovalent group from an oxoacid or group

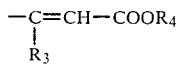

in which

R$_3$ represents hydrogen atom, a lower alkyl group or phenyl group and R$_4$ represents an alkyl group;

when n is 2, R$_2$ represents carbonyl group, an aliphatic or aromatic diacyl group, an alkylene group, an alkenylene group, an alkynylene group, an aralkylene group, a N-substituted dicarbamoyl group or a divalent group from an oxoacid;

when n is 3, R$_2$ represents an aromatic triacyl group or a trivalent group from an oxoacid; and when n is 4, R$_2$ represents an aromatic tetraacyl group, and A represents a group

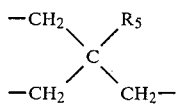

in which

R$_5$ represents hydrogen atom or a lower alkyl group or, when n is 1, R$_5$ may represent together with R$_2$ a group

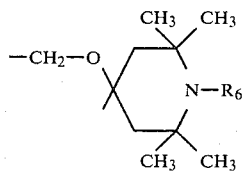

in which

R$_6$ represents the same group as defined in R$_1$ and may be the same or different from R$_1$, or a group

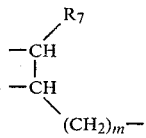

in which m is 1 or 2 and R$_7$ represents hydrogen atom or, when n and m are 1, R$_7$ represents methylene group together with R$_2$.

Murayama et al U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al U.S. Pat. No. 3,941,744, patented Mar. 2, 1976 disclose another variation of the piperidino spiro derivatives having the formula:

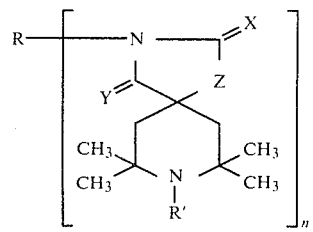

wherein

R' represents an alkyl group, a substituted alkyl group, an acyl group, an alkoxycarbonyl group, a substituted alkoxycarbonyl group, an amino group, a substituted amino group or nitroso group;

X represents oxygen atom or sulfur atom;

Y represents oxygen atom, sulfur atom or a group of the formula=N—R" in which R" is hydrogen atom, an alkyl group or a substituted alkyl group;

Z represents oxygen atom or a group of the formula >N—R''' is hydrogen atom, an alkyl group or a substituted alkyl group;

n is an integer of 1 through 4 inclusive; and

R represents, when n is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when n is 2, an alkylene group, an alkenylene group, an arylene group, a substituted arylene group, an aralkylene group, an alkylenediphenylene group, a bis-(acyloxyalkylene)-group, an alkylene-bis-(oxycarbonylalkyl)group, a dialkylene ether group or a diphenylene ether group, when n is 3, an alkanetriyl group, a tris-(acyloxyalkylene)-group, an alkane-tris-(oxycarbonylalkyl) group or a group of the group

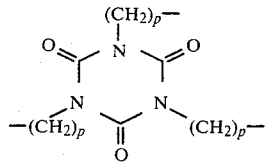

in which p is an integer of 1 through 8 inclusive, and when n is 4, an alkane tetrayl group, a tetrakis-(acyloxyalkylene) group or an alkanetetrakis-(oxycarbonylalkyl)group.

Murayama et al U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

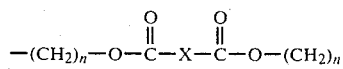

in which n is an integer of 1 or 2 and X is an alkylene group, or o-, m- or p-phenylene group or the carbon atoms of CO groups may be directly joined in the absence of X or a group of the formula:

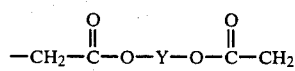

in which

Y is an alkylene group or o-, m- or p-phenylene group.

Ramey et al U.S. Pat. Nos. 3,899,491, patented Aug. 12, 1975 and 3,920,659, patented Nov. 18, 1975, disclose alkyl alkanoate derivatives of substituted piperizines and substituted piperazinodiones. The substituted piperazines of U.S. Pat. No. 3,899,491 have the formula:

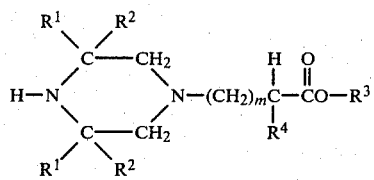

wherein $R^1$ and $R^2$ are methyl or together with the carbon to which they are bound form a mono-cyclic ring system having five or six carbon atoms;

$R^3$ is an alkyl group of from one to twenty atoms;

$R^4$ is hydrogen or methyl, and m is 0 or 1.

The substituted piperazinodiones of U.S. Pat. No. 3,920,659 have the formula:

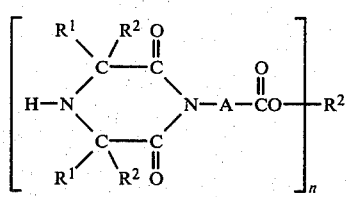

wherein $R^1$ and $R^2$ are independently of each other methyl or ethyl or together with the carbon to which they are bound form a cyclopentyl or cyclohexyl ring, which is unsubstituted or substituted with a methyl group;

n is an integer of from 1 to 2;

when n is 1, $R^3$ is an alkyl group of from one to twenty carbon atoms;

when n is 2, $R^3$ is an alkylene group of from two to eight carbon atoms; and

A is a straight or branched chain (lower) alkylene group containing from one to six carbon atoms with the limitation that the terminals of said alkylene group bear only hydrogen or one (lower) alkyl group.

Ramey et al U.S. Pat. No. 3,920,661, patented Nov. 18, 1975 disclose dicarboxylic acids and salts in which one carboxylic acid group is esterified with a 2,2,6,6-tetrasubstituted-4-hydroxy piperidine and having the formula:

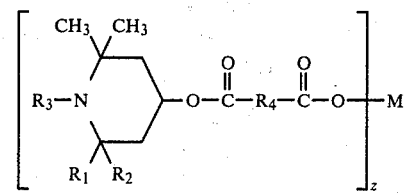

wherein $R_1$ and $R_2$ independently of each other are straight- or branched-chain alkyl having from one to six carbon atoms, or together with the carbon to which they are bound form a cyclopentyl or cyclohexyl ring, which is unsubstituted or substituted with a methyl group;

$R_3$ is hydrogen, alkyl having from one to twelve carbon atoms, β-methoxyethyl, alkenyl having three or four carbon atoms, propargyl, benzyl or alkyl-substituted benzyl;

$R_4$ is straight or branched-chain alkylene having five to eight carbon atoms, or the group $(CH_2)_mY(CH_2)_n$ wherein Y is oxygen or sulfur and m and n independently of each other are an integer from 1 to 3;

M is hydrogen or a metal selected from the group consisting of barium, nickel, manganese, calcium, zinc, iron, sodium, cobalt, tin, and dialkyl tin, and z has a value of from 1 to 4, the value of z being the same as the available valence of M.

Ramey et al U.S. Pat. No. 3,939,163 patented Feb. 17, 1976 disclose closely similar compounds in which $R_4$ is alkylene having from one to four carbon atoms.

Randell et al U.S. Pat. No. 3,939,170 patented Feb. 17, 1976 disclose dehydropyridinyl sulfides, sulfoxides and sulfones having the formula:

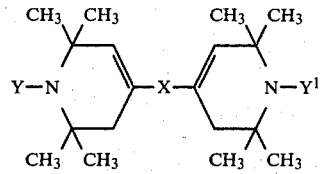

wherein

X is S, SO or $SO_2$ and Y and $Y^1$ are the same or different and each is H, OH, O— or a straight- or branched-alkyl residue having from one to four carbon atoms, and salts thereof when Y and $Y^1$ are other than O—.

Randell et al in published U.S. patent application No. B408,123 published Apr. 13, 1976 disclose substituted piperidine-4-ols having the formula:

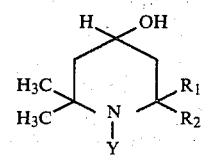

wherein $R_1$ and $R_2$ are the same or different and each is a straight- or branched-alkyl residue having from one to twelve carbon atoms, or $R_1$ and $R_2$, together with the carbon atom to which they are attached, form a cycloalkyl residue having from five to twelve carbon atoms or the group:

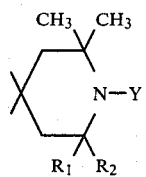

wherein

R₁ and R₂ have their previous significance and Y is a straight- or branched-alkyl residue having from one to twenty carbon atoms, an alkenyl or alkynyl residue having from three to twenty carbon atoms, an aralkyl residue having from seven to twelve carbon atoms or the group —CH₂X wherein X is the group

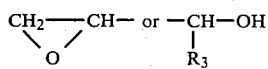

wherein

R₃ is hydrogen, a methyl or phenyl residue, the group

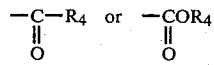

wherein

R₄ is an alkyl residue having from one to twenty carbon atoms.

Cook U.S. Pat. No. 3,929,804 patented Dec. 30, 1975 discloses 4-piperidine acetamide compounds having the formula:

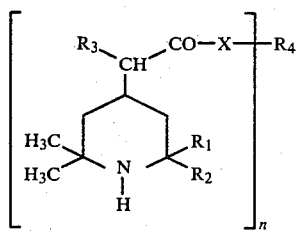

wherein

R₁ and R₂ are the same or different and each is a straight- or branched-alkyl residue having from one to twelve carbon atoms, or R₁ and R₂, together with the carbon atom to which they are attached form a cycloalkyl group having from five to twelve carbon atoms;

R₃ is hydrogen, a straight- or branched-alkyl residue having from one to four carbon atoms, an aralkyl residue having from seven to nine carbon atoms or a cycloalkyl group having from five or six carbon atoms;

R₄ is a metal ion or a hydrocarbyl residue having from two to twenty carbon atoms and being either unsubstituted or substituted by halogen or interrupted by one or more oxygen or sulphur atoms;

X is —O—, —S—, or >NR₅, wherein R₅ has the same significance as R₃; and n is 2, 3 or 4; as well as salts of the amine function of the compounds of formula I.

Cook U.S. Pat. No. 3,939,168 patented Feb. 17, 1976 discloses closely similar compounds having a Y substituent on the piperidyl nitrogen atom, Y being alkyl, alkenyl, aralkyl or a group

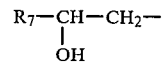

wherein

R₇ is hydrogen, alkyl or phenyl.

Randell et al U.S. Pat. No. 3,939,170, patented Feb. 17, 1976 provides di-4-(3,4-dehydro-2,2,6,6-tetramethyl piperidinyl)sulphides, sulphoxides and sulphones having the formula:

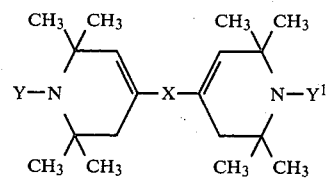

wherein

X is S, SO or SO₂, and Y and Y¹ are the same or different and each is H, OH, 0° or a straight- or branched-alkyl residue having from one to four carbon atoms, and salts thereof when Y and Y¹ are other than 0°.

Preferably X is S.

Smith et al U.S. Pat. No. 3,954,779, patented May 4, 1976 provides 4-(4'-hydroxycyclohexyl)-2,2,6,6-tetramethyl piperidines and derivatives thereof having the formula:

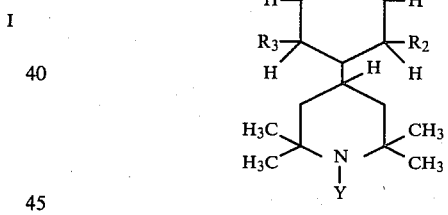

and salts thereof, wherein

R₁, R₂, R₃ and R₄ are the same or different and each is hydrogen, an alkyl residue having from one to nine carbon atoms, a cycloalkyl residue having from five to fourteen carbon atoms or a cycloalkyl-alkyl residue having from seven to fourteen carbon atoms;

Y is hydrogen;

O an alkyl residue having from one to four carbon atoms, or an aralkyl residue having from seven to twelve carbon atoms; and Z is hydrogen, an unsubstituted or substituted alkyl residue having from one to twenty carbon atoms, an alkenyl or alkynyl residue having from two to twenty carbon atoms, a cyclalkyl residue having from five to twelve carbon atoms, an aralkyl residue having from seven to twelve carbon atoms, an aryl residue having from six to twelve carbon atoms, or the group having the formula:

—COZ₁ wherein $Z_1$ has the same significance as Z as hereinbefore defined or $Z_1$ is a group $-NR_5R_6$
wherein
$R_5$ is hydrogen or an alkyl residue having from one to four carbon atoms and
$R_6$ is hydrogen, an alkyl residue having from one to twenty carbon atoms, a cycloalkyl residue having from five to twelve carbon atoms, an aralkyl residue having from seven to twelve carbon atoms or an aryl residue having from six to twelve carbon atoms.

Cook U.S. Pat. No. 3,959,291, patented May 25, 1976 provides derivatives of substituted 2-piperidinyl-4'-ethyl alcohol having the formula:

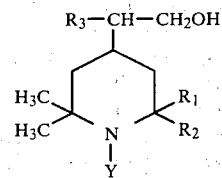

and salts thereof, wherein
$R_1$ and $R_2$ are the same or different and each is an alkyl residue having from one to twelve carbon atoms, or $R_1$ and $R_2$, together with the carbon atom to which they are bound, form a cycloalkyl residue having from five to twelve carbon atoms in the ring;
Y is O, hydrogen, a straight- or branched-alkyl residue having from one to twenty carbon atoms, an alkenyl or alkynyl residue having from three to twelve carbon atoms, an aralkyl residue having from seven to twelve carbon atoms or a group having the formula:

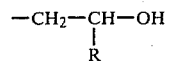

wherein
R is hydrogen, or a methyl or phenyl residue, and
$R_3$ is hydrogen, or a straight- or branched-chain alkyl residue having from one to twelve carbon atoms.

Cook U.S. Pat. No. 3,971,795, patented July 27, 1976 provides N-substituted piperidinylidene derivatives having the formula:

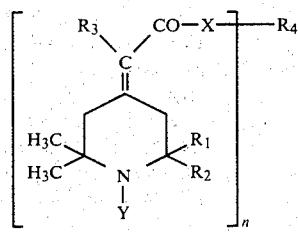

wherein
n is 1, 2, 3 or 4,
Y is hydrogen or a straight- or branched-alkyl residue having from one to twelve carbon atoms, an alkenyl residue having from three to twelve carbon atoms or an aralkyl residue having from seven to twelve carbon atoms and $R_1$ and $R_2$ are the same or different and each is a straight- or branched-alkyl residue having from one to twelve carbon atoms, or $R_1$ and $R_2$ together with the carbon atom to which they are attached form a cycloalkyl group having from five to twelve carbon atoms;

$R_3$ is hydrogen, a straight- or branched-alkyl residue having from one to four carbon atoms, an aralkyl residue having from seven to twelve carbon atoms, a cycloalkyl group having five or six carbon atoms;
$R_4$ is a hydrocarbyl residue having from one to twenty carbon atoms being either unsubstituted or substituted by halogen, or interrupted by one or more oxygen or sulphur atoms or $R_4$ is a metal ion, or, when n is 1, $R_4$, in addition, is hydrogen or has the structure:

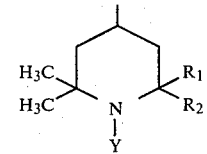

wherein
Y, $R_1$ and $R_2$ have their previous significance,
X is $-O-$, $-S-$ or $>NR_5$
wherein
$R_5$ has the same significance as $R_3$ or when n is 1 in addition $R_5$ and $R_4$ together with the nitrogen atom to which they are bound form a heterocyclic residue from four to ten carbon atoms; as well as salts of the amine function of the compound of formula I.

Murayama et al U.S. Pat. No. 3,975,357, patented Aug. 17, 1976 provides 1-substituted piperidine derivatives having the formula:

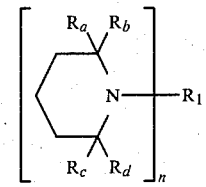

In the above formula, n represents 1 or 2.
$R_1$ represents when n=1, oxyl radical, hydroxy group, an alkyl group, a substituted alkyl group, an alkenyl group, an alkynyl group, an aralkyl group, a substituted aralkyl group or an acyl group,
when n=2, an alkylene group (the alkylene chain may optionally be interrupted by an oxygen atom), 2-butenylene group, a group of the formula $-CH_2COO-R_7-O-COCH_2-$ wherein
$R_7$ represents an alkylene group or xylylene group, or a group of the formula $-CH_2CH_2-OCO-R_8)_mCOO-CH_2CH_2-$ wherein
m represents 0 or 1,
$R_8$ represents an alkylene group (the alkylene chain may optionally be interrupted by a sulfur atom), an alkenylene group, phenylene group or 1,4-cyclohexylene group.

$R_a$ and $R_b$ represent methyl group or $R_a$ and $R_b$ together with carbon atom to which they are attached, form cyclohexyl group.
$R_c$ represents methyl group.
$R_d$ represents an alkyl group having one to five carbon atoms.
$R_c$ and $R_d$ together with carbon atom to which they are attached, may form cyclopentyl group, cyclohexyl group, a group of the formula:

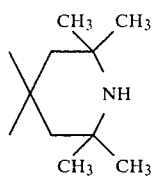

or a group of the formula

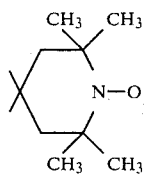

Murayama U.S. Pat. No. 3,975,462, patented Aug. 17, 1976 provides piperidine-spiro-hydantoin derivatives having the formula:

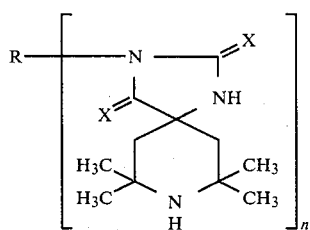

In the above formula (I), X represents oxygen atom or sulfur atom; n is an integer of 1 to 4 inclusive; and R represents when n is 1, an alkenyl group which may be substituted with halogen, an alkynyl group which may be substituted with phenyl, an aralkyl group which may be substituted with halogen, alkyl of one to four carbon atoms or halomethyl, a hydroxyalkyl group, an alkoxyalkyl group, an alkenyloxyalkyl group, an aryloxyalkyl group, an alkylthioalkyl group, an acyloxyalkyl group, an epoxyalkyl group, an N- alkyl-substituted aminoalkyl group, an alkoxycarbonyl alkyl group, an aryloxycarbonylalkyl group, an aliphatic acyl group, an alkoxycarbonyl group, a phosphino group which is substituted with phenoxy or alkoxy or a phosphinyl group which is substituted with phenoxy or alkoxy, when n is 2, an alkenylene group of four to eighteen carbon atoms, a dialkylene ether group, an aralkylene group, a bis-(acyloxyalkylene)group, or an alkylene-bis-(oxycarbonylalkyl) group, when n is 3, a tris-(acyloxyalkylene) group, an alkanetris-(oxycarbonylalkyl) group or a group of the formula:

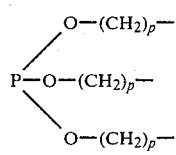

in which
p is an integer of 1 to 8 inclusive and p's may be the same or different, and
when n is 4, a tetrakis (acyloxyalkylene) group.

Avar et al U.S. Pat. No. 3,976,658, patented Aug. 24, 1976 provides pyrazole derivatives of the formula:

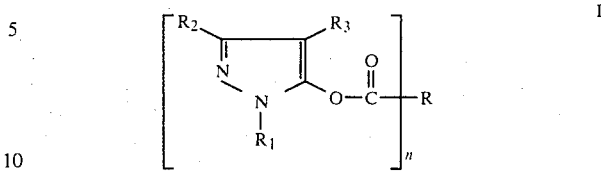

in which $R_1$ is a $C_{1-22}$ alkyl radical, a $C_{5-12}$ cycloalkyl radical, a $C_{6-12}$ cycloalkylalkyl radical, a $C_{7-12}$ aralkyl radical, of which the alkyl radical and the alkyl moiety of the cycloalkyl-alkyl radical are uninterrupted or interrupted by one or two sulphur atoms or by —COO—, and the aryl nucleus of the aralkyl radical is unsubstituted or substituted by a hydroxyl group and/or 1 or 2 $C_{1-12}$ alkyl radicals, or a phenyl group, unsubstituted or substituted by one or more substituents selected from one or two halogen atoms, a cyano group, a hydroxyl group, 1 or 2 $C_{1-12}$ alkyl radicals, 1 or 2 $C_{1-12}$ alkoxy radicals, a phenyl group and the radicals $R_4$—O— and $R_4$—$SO_2$—, wherein $R_4$ is a phenyl group, unsubstituted or substituted by 1 or 2 $C_{1-8}$ alkyl radicals, $R_2$, independently of $R_1$, has one of the significances of $R_1$, or is a cyano group or the radical —$COOR_5$, wherein $R_5$ is a $C_{1-12}$ alkyl radical, a $C_{5-12}$ cycloalkyl radical, a $C_{6-12}$ cycloalkylalkyl radical or a phenyl group, unsubstituted or substituted by a hydroxyl group and/or 1 or 2 $C_{1-8}$ alkyl radicals.

$R_3$ is a hydrogen atom or one of the significances of $R_1$, —$COR_1$ or —$COOR_5$, n is 1, 2 or 3, and R, when n is 1, is a phenyl group unsubstituted or substituted by a total of up to 3 substituents selected from one hydroxyl group, one to three halogen atoms, one phenyl group, one benzyl group, one phenoxy group, one to three alkyl radicals each containing one to eight carbon atoms and the sum of the carbon atoms not exceeding twelve, and one to three alkoxy radicals each containing one to twenty-two carbon atoms and the sum of the carbon atoms not exceeding twenty-two, or a monovalent naphthalene radical, or a monovalent radical of thiophene, benzothiophene, dibenzothiophene, furan, benzofuran, or dibenzofuran, and when n is 2, is a phenylene group, unsubstituted or substituted by a $C_{1-4}$ alkyl radical and/or a halogen atom, or a divalent naphthalene radical, or a divalent radical of thiophene or dibenzofuran, and when n is 3, is a 1,3,5-trivalent benzene radical.

Murayama et al, U.S. Pat. No. 4,061,616 patented Dec. 6, 1977, provides piperidyl derivatives having the following formula (I) or an acid addition salt thereof:

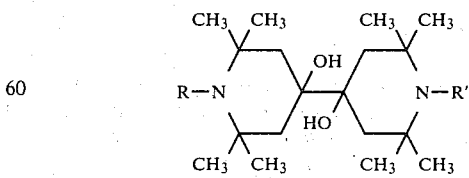

wherein

R and R', which may be the same or different, and each represents hydrogen atom, an alkyl group, an alkenyl group, an alkynyl group, an aralkyl group, a hydroxyalkyl group, an alkoxyalkyl group, an aliphatic or aromatic acyloxyalkyl group, a cyanoalkyl group, a halogenoalkyl group, an epoxyalkyl group, an alkoxycarbonylalkyl group, an aliphatic acyl group, an alkoxycarbonyl group or an aralkoxycarbonyl group.

Hillard et al U.S. Pat. No. 4,064,102 discloses 2,2,6,6-tetramethylpiperidine-4-carboxylic acid ester compounds having the formula:

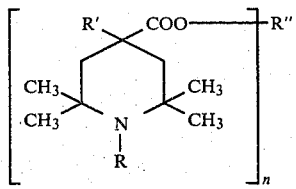

where

R is hydrogen or alkyl ($C_1$-$C_8$); R' is hydrogen, hydroxyl or alkoxy ($C_1$-$C_8$); R'' is alkyl ($C_1$-$C_{20}$), alkylene ($C_2$-$C_{12}$), cycloalkyl, wherein the cycloaliphatic ring contains 5- or 6-carbon atoms, cycloalkylene, wherein the cycloaliphatic ring may contain lower alkyl substituents, arylene, aralkylene and alkenyl ($C_3$-$C_{20}$); n is an integer from 1 to 4.

Murayama U.S. Pat. No. 4,066,615, patented Jan. 3, 1978, provides stabilizers having the formula:

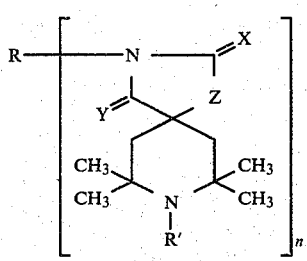

wherein:

R' represents an alkyl, an acyl, an alkoxycarbonyl, an amino or nitroso group;

X represents oxygen or sulfur;

Y represents oxygen, sulfur or a group of the formula =N-R'' in which R'' is hydrogen or alkyl;

Z represents oxygen or a group of the formula >N-R''' in which R''' is hydrogen or alkyl;

n is an integer of 1 to 4; and

R represents, when n is 1, alkyl, aryl, cycloalkyl, alkoxycarbonyl, substituted phosphino or substituted phosphinyl, when n is 2, alkylene, alkenylene, arylene, aralkylene; alkylenediphenylene, bis-(carboxycarbonyl)alkylene, alkylene-bis-(oxycarbonylalkyl), dialkylene ether or diphenylene ether, when n is 3, alkanetriyl, tris-(alkoxycarbonyl)alkanetriyl, alkanetriyl-tris-(oxycarbonylalkyl) or a group of the formula

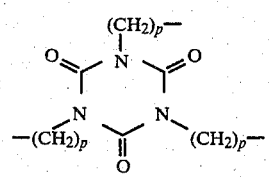

in which p is an integer of 1 through 8 inclusive, and, when n is 4, alkanetetrayl, tetrakis-(alkoxycarbonyl)alkanetetrayl or alkanetetrayl-tetrakis-(oxycarbonylalkyl).

Soma et al U.S. Pat. No. 4,097,587 patented June 27, 1978 provides 7,7,9,9-tetra-substituted-1,3,8-triazaspiro[4.5]decane-2,4-diones having an alkyl or allyl group at either the 6- or the 10-position which are said to be useful for the stabilization of polymers against photo- and thermal-deterioration.

These compounds have the formula:

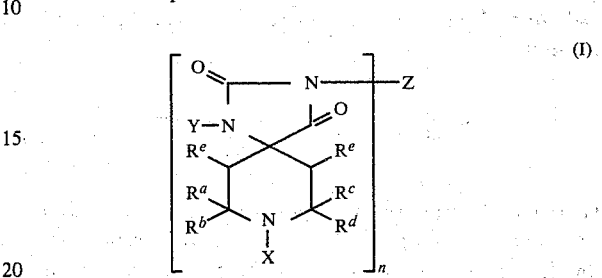

wherein:

$R^a$ represents a methyl group;

$R^b$ represents a lower alkyl group;

$R^c$ represents an alkyl group;

$R^d$ represents an alkyl group, a phenyl group or an aralkyl group; or $R^c$ and $R^d$, together with the carbon atom to which they are attached, represent a cycloalkyl group;

one of $R^e$ and $R^{e'}$ represents a hydrogen atom and the other of $R^e R^{e'}$ represents a lower alkyl group or an allyl group;

n is 1 or 2;

Y represents a hydrogen atom or, when either X nor Z represents a hydrogen atom, Y represents a hydrogen atom, a methyl group, an ethyl group, an allyl group or a benzyl group;

X represents a hydrogen atom, an oxyl radical, a lower alkyl group, an alkenyl group, a benzyl group, a 2,3-epoxypropyl group or a group of formula —$CH_2$C-$H_2OR^1$ (wherein $R^1$ represents a hydrogen atom or an aliphatic, aromatic, aralkyl or alicyclic acyl group);

when n=1:

Z represents a hydrogen atom, an alkyl group, an alkenyl group, an aralkyl group which is unsubstituted or has one or more substituents in its aryl moiety, an aryl group which is unsubstituted or has one or more chlorine and/or methyl substituents, a cyclohexyl group, a 2,3-epoxypropyl group, an alkoxyalkyl group, a phenoxyalkyl group, a group of formula —$CH_2COOR^2$ (wherein $R^2$ represents an alkyl group or a phenyl group) or a group of formula

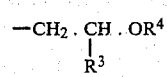

(wherein $R^3$ represents a hydrogen atom, a methyl group or a phenyl group, and $R^4$ represents a hydrogen atom or an aliphatic aromatic, aralkyl or alicyclic acyl group);

when n=2:

Z represents an alkylene group, which is optionally interrupted by an oxygen atom, a 2-butenylene group, a xylylene group; an arylene group which is unsubstituted or has one or more methyl substituents, a group of formula

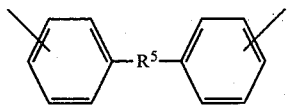

(wherein $R^5$ represents an oxygen atom or a methylene group), a group of formula $-CH_2.COOR^6OCO.CH_2-$ (wherein $R^6$ represents an alkylene group) or a group of formula

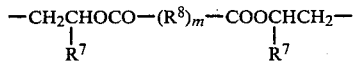

(wherein $R^7$ represents a hydrogen atom, a methyl group or a phenyl group, m is 0 or 1 and $R^8$ represents an alkylene group optionally interrupted by a sulphur atom, an alkylene group, a phenylene group or a 1,4-cyclohexylene group); and acid addition salts thereof.

Mayer et al U.S. Pat. No. 4,097,452 patented June 27, 1978 provides diazadispiro-hexadecane compounds having the formula:

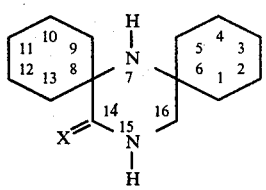

wherein X means=O,=NH or

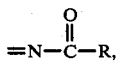

R being an alkyl group with one to seventeen carbon atoms, preferably the methyl group, for the stabilization of organic matter against the decomposition by light and heat.

Minagawa et al U.S. Pat. No. 4,136,081, patented Jan. 23, 1979, provides 2,2,6,6-tetramethyl-4-piperidyl alcohol esters of aliphatic tetracarboxylic acids, useful as stabilizers for organic polymeric materials, and having the general formula:

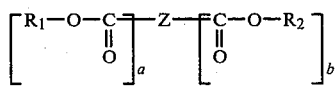

wherein:
$R_1$ is selected from the group consisting of

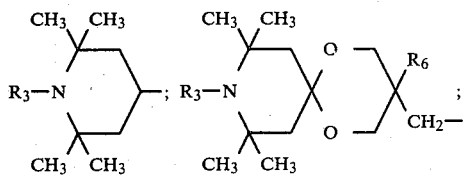

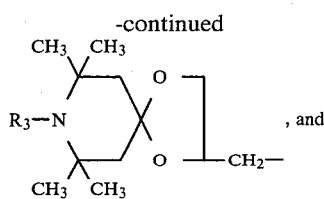

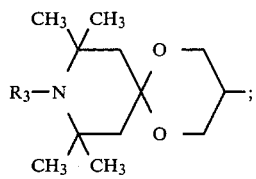

and when a is 2, 3, or 4, the $R_1$ groups can be the same or different, $R_2$ is selected from the group consisting of hydrogen, alkyl, alkenyl, cycloalkyl, alkcycloalkyl, cycloalkalkyl, aryl, aralkyl, and alkaryl; and when b is 2, or 3, the $R_2$ groups can be the same or different;

$R_3$ is selected from the group consisting of hydrogen and O;

$R_6$ is lower alkyl;

a is selected from the group consisting of 1, 2, 3 and 4;

b is selected from the group consisting of 0, 1, 2 and 3;

a+b is equal to 4; and

Z is a tetravalent aliphatic or cycloaliphatic radical carrying four

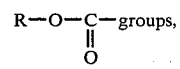

where R is $R_1$ or $R_2$, and can include from one to three hydroxyl groups OH.

In accordance with the instant invention, 2,2,6,6-tetraalkyl-4-piperidyl alchol esters of tetradecylene polycarboxylic acids are provided, useful as stabilizers for organic polymeric materials, and having the general formula:

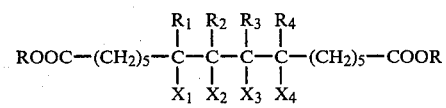

in which:
R is selected from the group consisting of

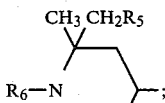

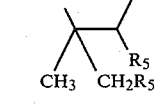

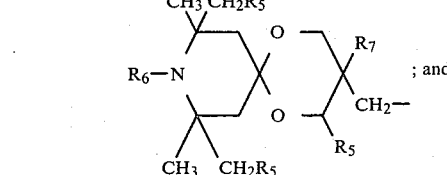

-continued

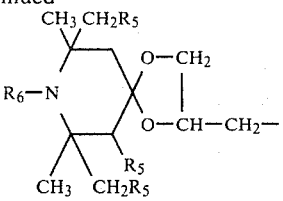

wherein:

R₅ and R₆ are each hydrogen or lower alkyl or hydroxyalkyl having from one to about six carbon atoms;

R₇ is lower alkyl having from one to about six carbon atoms;

R₁, R₂, R₃ and R₄ are selected from the group consisting of hydrogen and methyl;

X₁ and X₂ are selected from the group consisting of hydrogen and COOR;

X₂ and X₄ are selected from the group consisting of COOR and

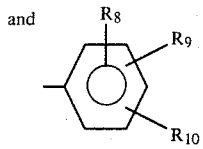

wherein:

R₈; R₉ and R₁₀ are selected from the group consisting of hydrogen, hydroxy, alkyl, and alkoxy having from one to about eighteen carbon atoms.

The tetradecylene radical

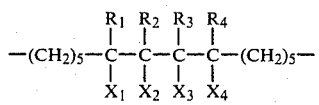

has from fourteen to about eighty-six carbon atoms in a straight or branched saturated aliphatic chain, with from two to six carboxylic acid ester groups COOR and up to two

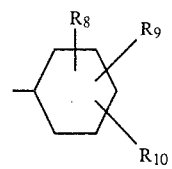

groups. Exemplary are tetradecylene, 6-methyl tetradecylene, 6,7-dimethyl tetradecylene, 6,7,8-trimethyl tetradecylene, and 6,7,8,9-tetramethyl tetradecylene with two to six COOR.

The tetradecylene radical is derived from a polycarboxylic aliphatic or aliphatic aromatic acid, which is readily prepared by chain-opening dimerization of cyclohexanone in the presence of an unsaturated carboxylic acid or ester thereof such as acrylic acid, methacrylic acid, crotonic acid or maleic acid, or in the presence of styrene derivatives such as styrene, α-methylstyrene, hydroxystyrene or vinyltoluene, as described for example in Kagaku Kogyo Nippo, Mar. 13, 1975 and Kagaku Kogyo Jiho, No. 1682, June 15, 1979.

Exemplary R₅ and R₆ lower alkyl include methyl, ethyl, propyl, isopropyl, butyl, isobutyl, sec-butyl, amyl, isoamyl, tert-amyl, hexyl, isohexyl and tert-hexyl.

Exemplary R₅ and R₆ hydroxyalkyl include hydroxymethyl, hydroxyethyl, hydroxypropyl, hydroxybutyl, hydroxyamyl and hydroxyhexyl.

Exemplary R₈, R₉ and R₁₀ alkyl radicals include methyl, ethyl, propyl, isopropyl, butyl, isobutyl, sec-butyl, t-butyl, amyl, t-amyl, hexyl, octyl, t-octyl, nonyl, decyl, dodecyl and octadecyl.

Exemplary R₈, R₉ and R₁₀ alkoxy radicals include oxymethyl, oxyethyl, oxypropyl, oxyisopropyl, oxybutyl, oxyisobutyl, sec-oxybutyl, t-oxybutyl, oxyamyl, t-oxyamyl, oxyhexyl, oxyoctyl, t-oxyoctyl, oxynonyl, oxydecyl, oxydodecyl and oxyoctadecyl.

The following compounds are exemplary:

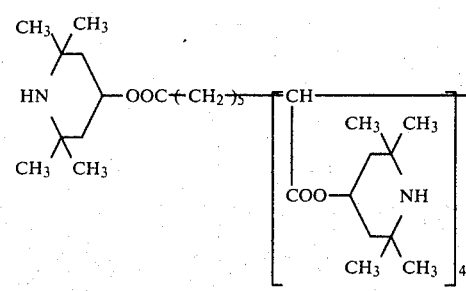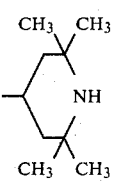 1.

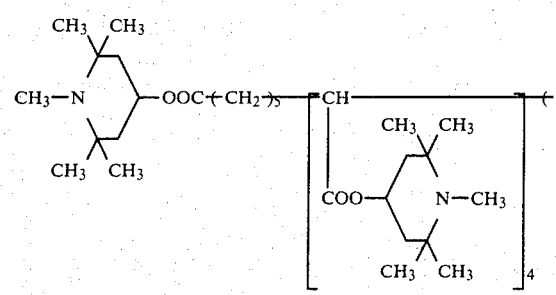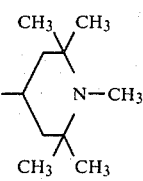 2.

-continued
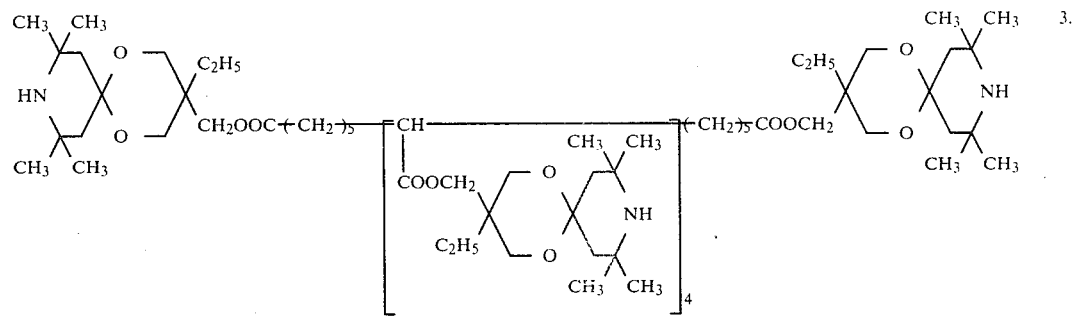
3.
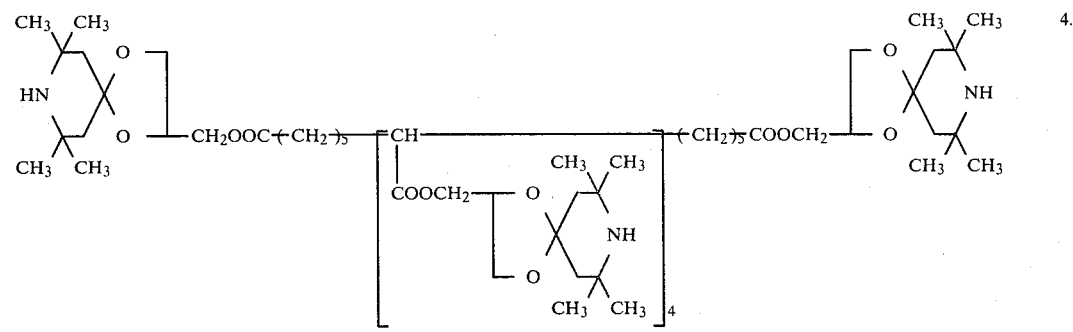
4.
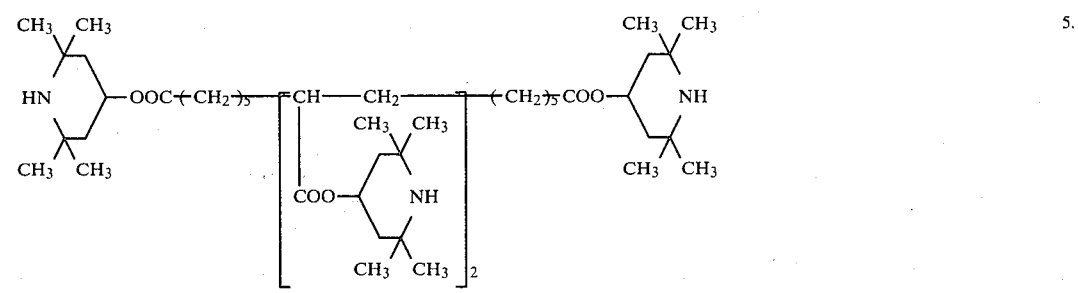
5.
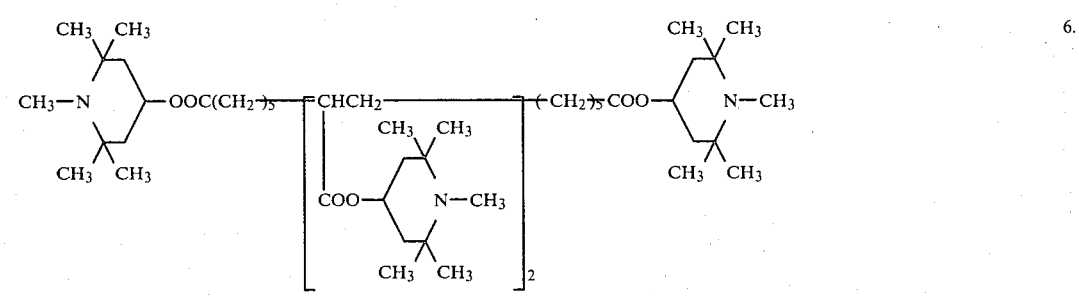
6.
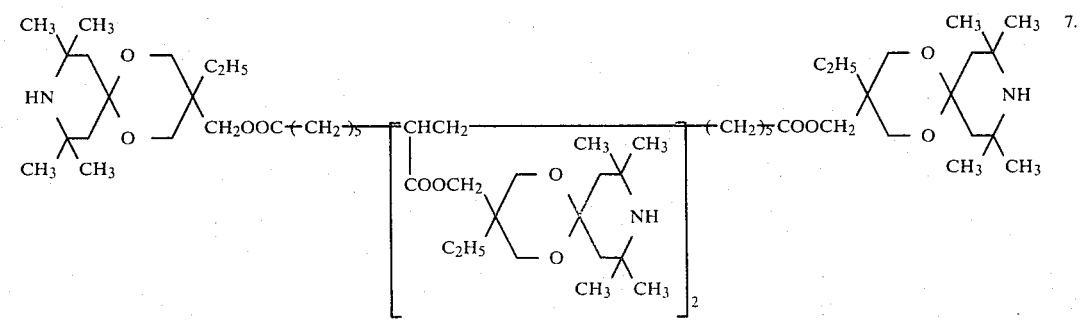
7.

-continued
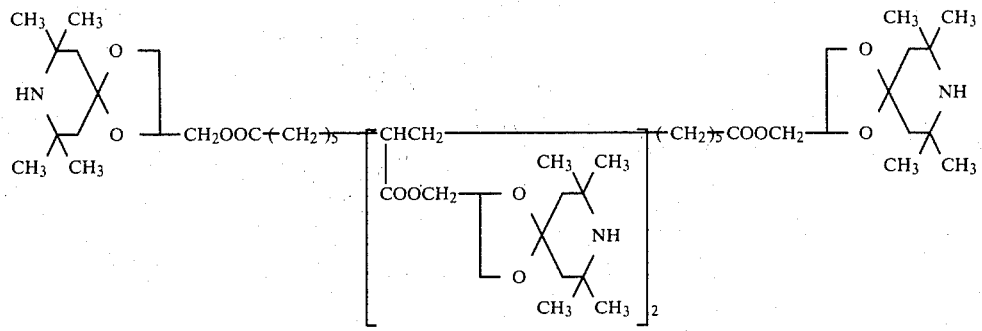
8.
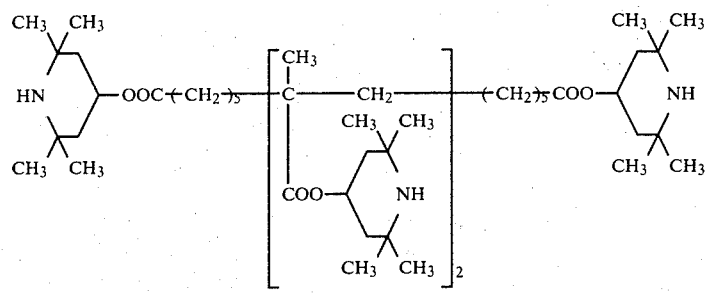
9.
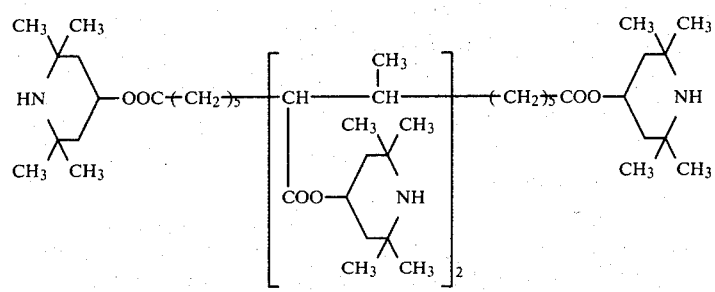
10.
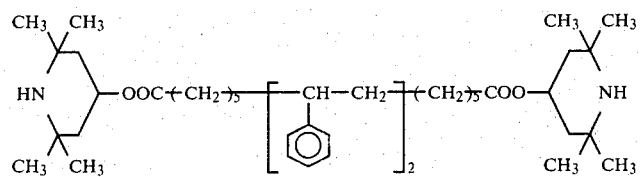
11.
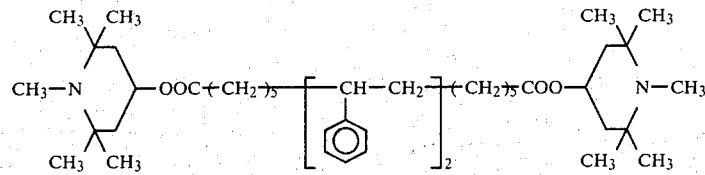
12.
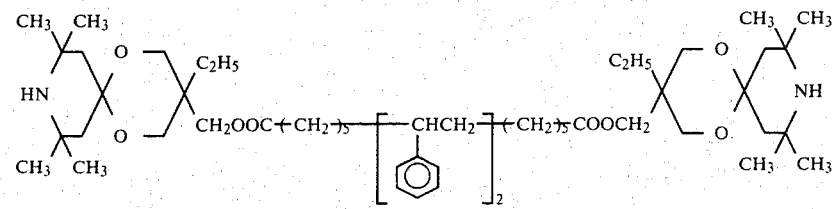
13.

-continued
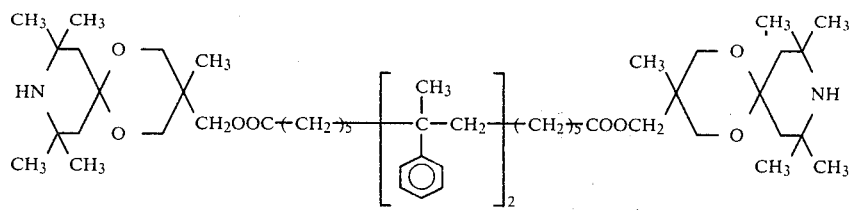
14.
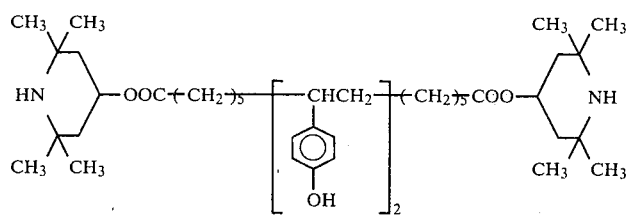
15.
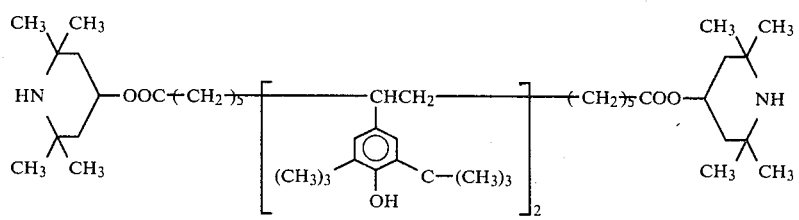
16.
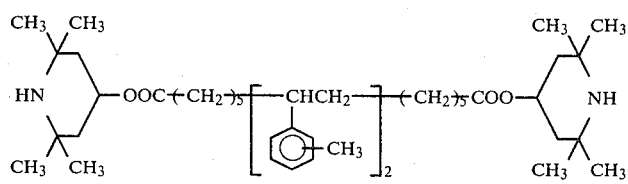
17.
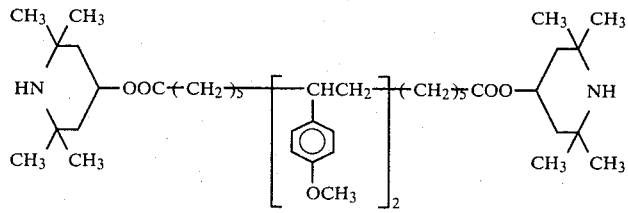
18.
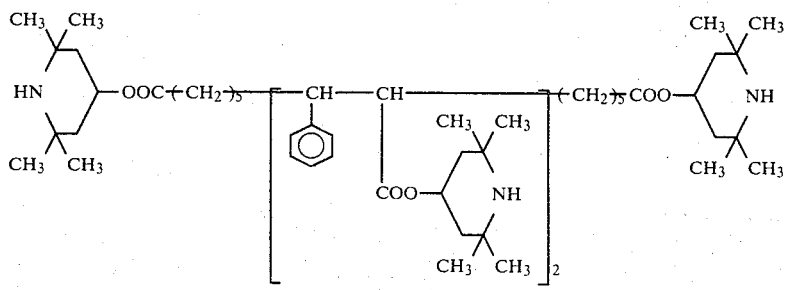
19.

-continued

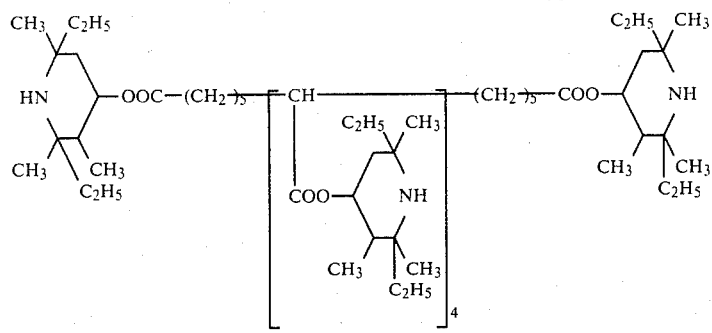

20.

These compounds are readily prepared by reaction of the corresponding piperidinyl alcohol:

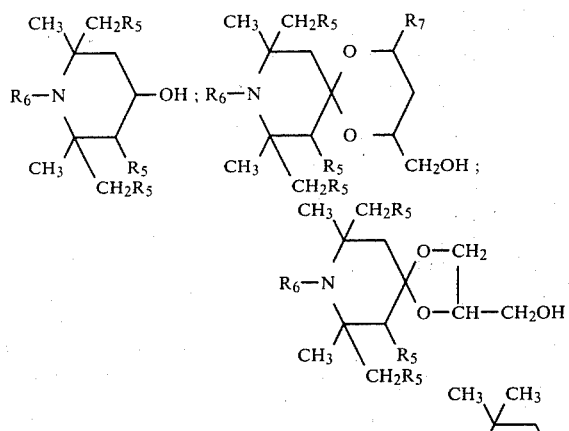

with the long chain aliphatic carboxylic acid ester or acid halide. The hydroxy group of the piperidine becomes esterified with the carboxylic acid groups, displacing any esterifying radicals, and forming the 4-piperidinyl alcohol tetradecylene polycarboxylic acid ester of the invention:

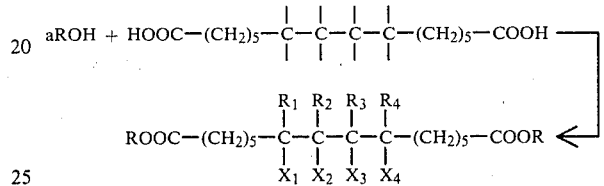

The following Examples illustrate the preparation of the compounds of the invention.

EXAMPLE I

Preparation of

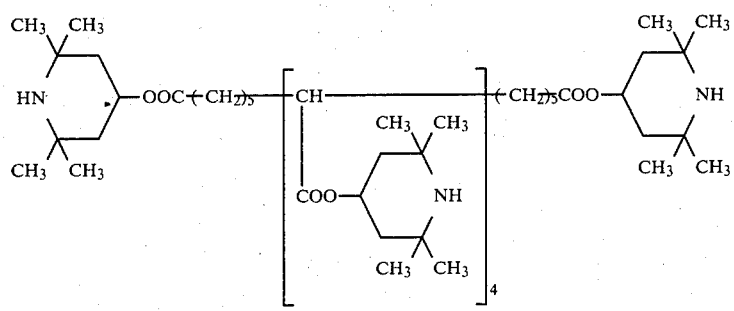

10.9 g of 1,6,7,8,9,14-Tetradecane hexacarboxylic acid hexamethyl ester, 19.8 g of 2,2,6,6-tetramethyl-4-piperidinol and 1.5 g tetraisopropyl titanate were dissolved in 50 ml of xylene.

The whole was heated and stirred for ten hours at 130° to 140° C. under a stream of nitrogen. After cooling, 50 ml of xylene was added, the mixture washed with water and then dried. The solvent was distilled off, and the residue was recrystallized from n-hexane. 20.3 g of white crystals were obtained. N Content:
Found: 6.33% Calculated: 6.48%
IR Analysis:
$\nu_{NH}$3325 cm$^{-1}$, $\nu_{c=o}$1730 cm$^{-1}$

EXAMPLE II

Preparation of

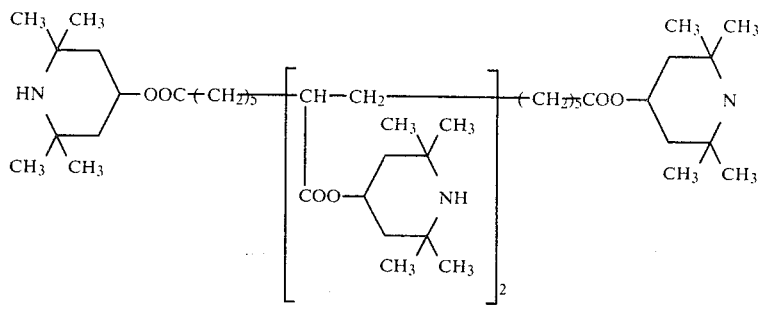

8.6 g of 1,6,8,14-Tetradecane tetracarboxylic acid tetramethyl ester, 13.2 g of 2,2,6,6-tetramethyl-4-piperidinol and 1.0 g of tetraisopropyl titanate were dissolved in 30 ml of xylene.

The whole was heated and stirred for eight hours at 130° to 140° C. under a stream of nitrogen. After cooling, the solution was recrystallized from n-hexane as in Example I. 15.5 g of white crystals were obtained.

N Content:
Found: 5.93% Calculated: 6.02%
IR Analysis:
$\nu_{NH}$ 3300 cm$^{-1}$, $\nu_{C=O}$ 1730 cm$^{-1}$ The 2,2,6,6-tetraalkyl-4-piperidyl tetradecylene carboxylic acid esters of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene, polystyrene; polydienes, such as polybutadiene and polyisoprene; and copolymers of olefins and dienes with other ethylenically and acetylenically unsaturated monomers, such as ethylene-propylene copolymers, ethylene-butene copolymers, ethylene-pentene copolymers, ethylene-vinyl acetate copolymers, styrene-butadiene copolymers, acrylonitrile-styrene-butadiene copolymers, synthetic rubbers of all types, such as polychloroprene; polyvinyl halides, including polyvinyl chloride homopolymer, polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycol-terephthalic acid ester polymers; polyamides such as polyepsiloncaprolactam; polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The 2,2,6,6-tetraalkyl-4-piperidyl tetradecylene carboxylic acid esters of the invention can be used as a stabilizer in an amount within the range from about 0.001 to about 5 parts by weight, preferably from 0.05 to 3 parts by weight, per 100 parts by weight of resin.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolefin resins there can be employed fatty acid salts of polyvalent metals, organic phosphites, phenolic antioxidants, and the higher fatty acid esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile-butadiene-styrene terpolymers, antioxidants such as hindered phenols and bisphenols, polyvalent metals salts of the higher fatty acids, and organic phosphites can be used.

In addition, other conventional additives for synthetic polymers, such as plasticizers, lubricants, emulsifiers, antistatic agents, flameproofing agents, pigments and fillers, can be employed.

The following Examples in the opinion of the inventors represent preferred embodiments of synthetic resin compositions in accordance with the invention.

EXAMPLES 1 TO 9

A group of polyvinyl chloride resin compositions were prepared, having the following formulation:

| Ingredient | Parts by Weight |
| --- | --- |
| Polyvinyl chloride | 100 |
| Dioctyl phthalate | 48 |
| Epoxydized soyabean oil | 2 |
| Tris-(nonylphenyl)phosphite | 0.2 |
| Ca stearate | 1.0 |
| Zn stearate | 0.1 |
| Stabilizer as shown in Table I | 0.2 |

This formulation was blended, and sheeted off on a two-roll mill to form sheets 1 mm thick. The color of these was observed, and the light resistance of these sheets was then determined by placing strips 1 cm long in a Weather-O-Meter, and exposing them to ultraviolet light. The time in hours was then noted for the sheets to develop a noticeable discoloration and/or embrittlement, indicating deterioration due to oxidation in the presence of ultraviolet light. The time is reported as hours to failure.

The following results were obtained:

TABLE I
| | Stabilizer | Hours to Failure |
|---|---|---|
| Control | | |
| 1 | None | 180 |
| 2 | Bis(2,2,6,6-tetramethyl-4-piperidyl)adipate | 330 |
| 3 | 2,2,6,6-Tetramethyl-4-piperidyl benzoate | 300 |
| 4 | Tetrakis(2,2,6,6-tetramethyl-4-piperidyl)-1,2,3,4-butane tetracarboxylate | 450 |
| Ex. No. | | |
| 1 | 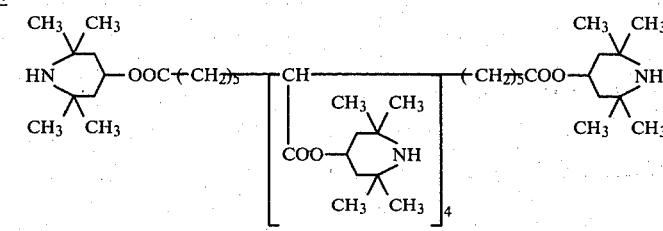 | 670 |
| 2 | 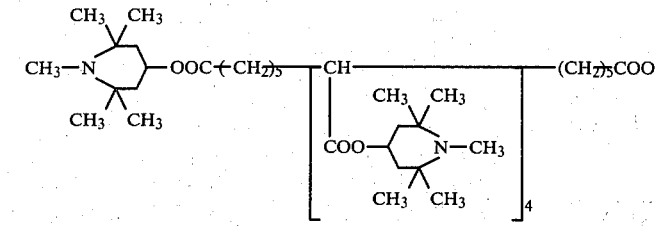 | 630 |
| 3 | 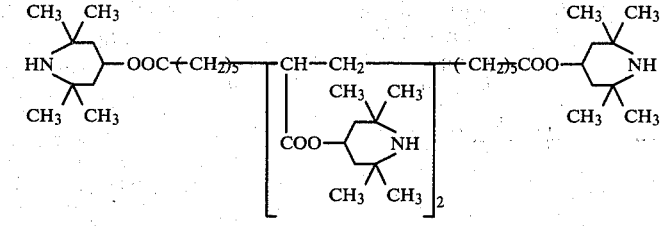 | 640 |
| 4 | 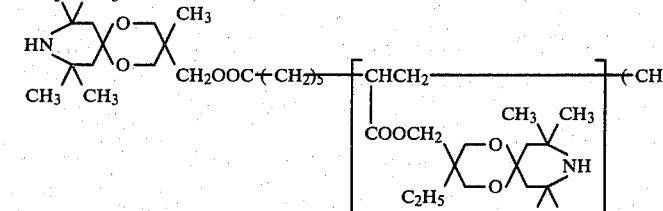 | 610 |
| 5 | 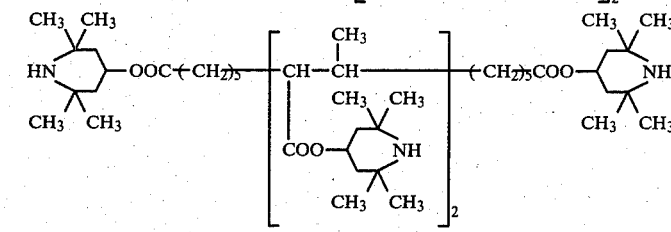 | 620 |
| 6 | 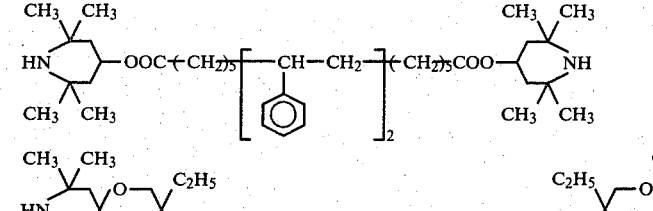 | 570 |
| 7 | 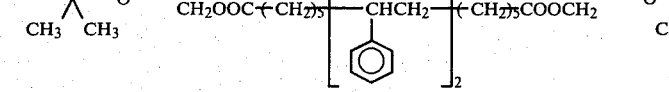 | 560 |

TABLE I-continued

| | Stabilizer | Hours to Failure |
|---|---|---|
| 8 | [structure: bis-piperidinyl ester with phenol-containing polymer backbone, n=2] | 590 |
| 9 | [structure: bis-piperidinyl ester with methylphenyl-containing polymer backbone, n=2] | 570 |

The stabilizers of the invention are clearly superior to the controls.

EXAMPLES 10 TO 18

A group of polypropylene compositions was prepared, using stabilizers of the invention and of prior art, and having the following formulation:

| Ingredient | Parts by Weight |
|---|---|
| Polypropylene | 100 |
| Stearyl-β-(3,5-di-t-butyl-4-hydroxy-phenyl) propionate | 0.2 |
| Stabilizer as shown in Table II | 0.3 |

The composition was blended in a Brabender Plastograph and then compression-molded to form sheets 0.3 mm thick. Pieces 2.5 cm square were cut off from the sheets and exposed to a high pressure mercury lamp with and without immersion in hot water at 88° C. for six and fifteen hours. The hours to failure were noted in comparison with two prior art stabilizers, and the results are shown in Table II.

TABLE II

| | Stabilizer | Without immersion | After immersion 6 hours | 15 hours |
|---|---|---|---|---|
| Control 1 | Bis(2,2,6,6-tetramethyl-4-piperidyl)-1,10-decane dicarboxylate | 470 | 400 | 310 |
| 2 | Bis(1,2,2,6,6-pentamethyl-4-piperidyl)-1,18-octadecane dicarboxylate | 420 | 370 | 300 |
| 3 | Bis(9-aza-3-ethyl-8,8,10,10-tetramethyl-1,5-dioxaspiro-[5,5]-3-undecylmethyl) sebacate | 430 | 360 | 280 |
| Ex. No. 10 | [structure: bis-piperidinyl ester with branched piperidinyl side chain, n=4] | 720 | 680 | 650 |
| 11 | [structure: bis-dioxaspiro-piperidinyl ester with branched side chain, n=4] | 690 | 660 | 620 |

TABLE II-continued

| | | Hours to failure | | |
|---|---|---|---|---|
| | | Without immersion | After immersion | |
| | Stabilizer | | 6 hours | 15 hours |
| 12 | [structure] | 650 | 630 | 600 |
| 13 | [structure] | 670 | 640 | 610 |
| 14 | [structure] | 650 | 620 | 610 |
| 15 | [structure] | 630 | 600 | 580 |
| 16 | [structure] | 620 | 590 | 560 |
| 17 | [structure] | 660 | 620 | 600 |
| 19 | [structure] | 680 | 630 | 590 |

The stabilizers of the invention are clearly superior to the controls.

Ethylene-vinyl acetate copolymer compositions were prepared using stabilizers of the invention and of the prior art, and having the following formulation:

| Ingredient | Parts by Weight |
|---|---|
| Ethylene-vinyl acetate copolymer | 100 |
| 2,6-di-t-butyl-p-cresol | 0.1 |
| Ca stearate | 0.1 |
| Zn stearate | 0.1 |
| Diisodecyl phenyl phosphite | 0.2 |
| Stabilizer as shown in Table III | 0.3 |

The composition was blended on a two-roll mill at 130° C. and sheets 0.4 mm thick were then compression molded at 140° C. from the resulting blend. Pieces 2.5 cm square were cut off from the sheets, and exposed to ultraviolet light in a Weather-O-Meter for 500 hours. At the start and at the conclusion of the test, the tensile strength of the sheet samples was determined. The results are given in Table III as percent retention of the initially-determined tensile strength.

TABLE III

| | Stabilizer | % Retention of tensile strength after 500 hours |
|---|---|---|
| Control | | |
| 1 | 2-Hydroxy-4-methoxy-benzophenone | 70 |
| 2 | Bis(2,2,6,6-tetramethyl-4-piperidyl) sebacate | 74 |
| 3 | 9-Aza-3-ethyl-8,8,10,10-tetramethyl-1,5-dioxaspiro [5,5]-3-undecylmethyl stearate | 67 |
| Ex. No. | | |
| 19 | (structure) | 82 |
| 20 | (structure) | 86 |
| 21 | (structure) | 81 |
| 22 | (structure) | 85 |
| 23 | (structure) | 85 |

TABLE III-continued

| | Stabilizer | % Retention of tensile strength after 500 hours |
|---|---|---|
| 24 | [structure: bis-piperidinyl-dioxaspiro compound with α-methylstyrene-type polymer linker] | 83 |
| 25 | [structure: bis-piperidinyl compound with 4-methoxybenzyl-substituted polymer linker] | 82 |

The stabilizers of the invention are clearly superior to the controls.

EXAMPLES 26 TO 34

High density polyethylene compositions were prepared using stabilizers of the invention and of prior art, having the following formulation:

| Ingredient | Parts by Weight |
|---|---|
| High density polyethylene | 100 |
| Tetrakis(methylene-3-(3,5-di-t-butyl-4-hydroxyphenyl)propionate)methane | 0.1 |
| Ca stearate | 1.0 |
| Distearyl thiodipropionate | 0.3 |
| Stabilizer as shown in Table IV | 0.3 |

The composition was blended on a two-roll mill and sheets 0.5 mm thick were prepared by compression molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table IV.

TABLE IV

| | Stabilizer | Hours to failure |
|---|---|---|
| Control | | |
| 1 | 2(2'Hydroxy-5'-methylphenyl)benzotriazole | 760 |
| 2 | Bis(9-aza-3-ethyl-8,8,10,10-tetramethyl-1,5-dioxaspiro [5,5]-3-undecylmethyl) adipate | 750 |
| 3 | Tetrakis(1,2,2,6,6-pentamethyl-4-piperidyl)-1,2,3,4-butane-tetracarboxylate | 920 |
| Ex. No. | | |
| 26 | [structure: bis-piperidinyl compound with tetra-branched piperidinyl ester linker] | 1460 |
| 27 | [structure: bis-piperidinyl-dioxaspiro (C2H5 substituted) compound with tetra-branched dioxaspiro-piperidinyl ester linker] | 1320 |

TABLE IV-continued

| | Stabilizer | Hours to failure |
|---|---|---|
| 28 | 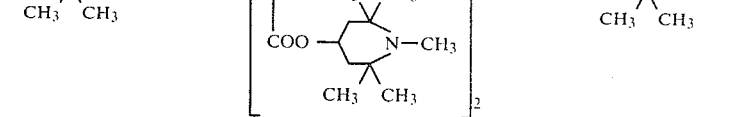 | 1340 |
| 29 | 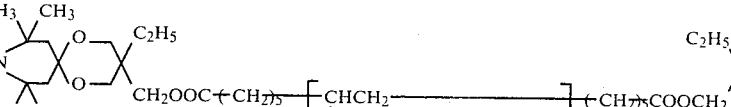 | 1350 |
| 30 | 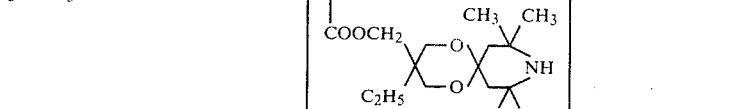 | 1300 |
| 31 | 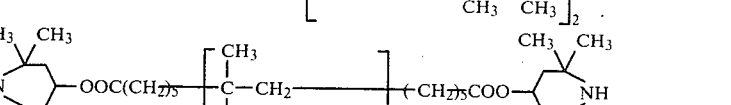 | 1250 |
| 32 | 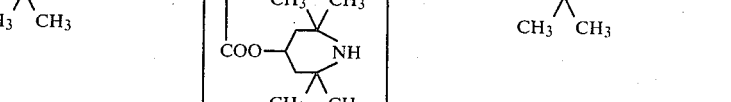 | 1220 |
| 33 | 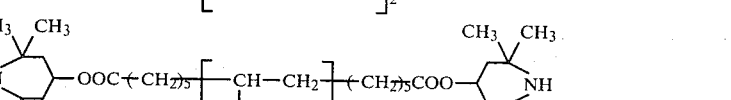 | 1260 |
| 34 | 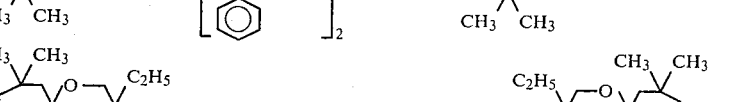 | 1410 |

The stabilizers of the invention are far superior to the controls.

EXAMPLES 35 TO 44

Acrylonitrile-butadiene-styrene terpolymer resin compositions were prepared, using stabilizers of the invention and of the prior art, and having the following formulation:

| Ingredient | Parts by Weight |
|---|---|
| Acrylonitrile-butadiene-styrene terpolymer | 100 |
| 4,4'-butylidene-bis(2-t-butyl-m-cresol) | 0.1 |
| Stabilizer as shown in Table V | 0.3 |

The composition was blended on a two-roll mill, and sheets 3 mm thick were prepared by compression molding of the resulting blend. Pieces 2.5 cm square were cut off from the sheets, and subjected to ultraviolet light in a Weather-O-Meter for 800 hours. Tensile strength before and after the text exposure was determined, and the results reported as percent of tensile strength retained, at the end of this time, in Table V.

TABLE V

| Control | Stabilizer | % Tensile strength retained |
|---|---|---|
| 1 | 2,4-Dihydroxy benzophenone | 55 |
| 2 | Bis(2,2,6,6-tetramethyl-4-piperidyl)-1,10-decane dicarboxylate | 58 |
| 3 | 2,2,6,6-tetramethyl-4-piperidyl-β-(3,5-di-t-butyl-4-hydroxyphenyl)propionate | 60 |

| Example No. | Structure | % |
|---|---|---|
| 35 | [structure] | 88 |
| 36 | [structure] | 87 |
| 37 | [structure] | 91 |
| 38 | [structure] | 86 |

TABLE V-continued

| | Stabilizer | % Tensile strength retained |
|---|---|---|
| 39 | [structure: bis(2,2,6,6-tetramethylpiperidinyl) ester with CH-CH(CH3) backbone and pendant piperidinyl COO group] | 89 |
| 40 | [structure: bis(2,2,6,6-tetramethylpiperidinyl) ester with -[CH-CH2]- phenyl-substituted backbone, subscript 2] | 86 |
| 41 | [structure: bis(2,2,6,6-tetramethylpiperidinyl) ester with -CHCH2- p-hydroxyphenyl-substituted backbone, subscript 2] | 83 |
| 42 | [structure: bis(2,2,6,6-tetramethylpiperidinyl) ester with -CHCH2- 3,5-di-tert-butyl-4-hydroxyphenyl-substituted backbone, subscript 2] | 85 |
| 43 | [structure: bis(2,2,6,6-tetramethylpiperidinyl) ester with -CHCH2- p-methoxyphenyl-substituted backbone, subscript 2] | 83 |
| 44 | [structure: bis(tetraethyl-dimethyl piperidinyl) ester with CH backbone and pendant piperidinyl COO group, subscript 4] | 86 |

The stabilizers of the invention are clearly superior to the controls.

EXAMPLES 45 TO 50

Conventional heat stabilizers for polymeric materials may lose their effectiveness because of volatilization or decomposition at high polymer processing temperatures. This is not true of the stabilizers of the invention, as shown by observing the effect of heat in repeated extrusions of ethylene-propylene copolymer compositions. These compositions were prepared using stabilizers of the invention and of the prior art, and having the following formulation:

| Ingredient | Parts by Weight |
|---|---|
| Ethylene-propylene copolymer | 100 |
| Ca stearate | 0.2 |
| Stearyl-β-(3,5-di-t-butyl-4-hydroxy-phenyl) propionate | 0.1 |
| Dilauryl thiodipropionate | 0.2 |
| Stabilizer as shown in Table VI | 0.2 |

The ingredients were mixed and the compositions then extruded to form compounds (cylinder temperature 230° C. and 240° C., head die temperature 25° C., velocity 20 rpm). The compositions were extruded five times, and the test pieces were molded by injection molding at 250° C. The test pieces were exposed to a high voltage mercury lamp, and the hours to failure noted as shown in Table VI.

TABLE VI

| | Stabilizer | Hours to failure Extruded 1 time | Hours to failure Extruded 5 times |
|---|---|---|---|
| Control | | | |
| 1 | Bis(2,2,6,6-tetramethyl-4-piperidyl)-1,10-decane-dicarboxylate | 420 | 250 |
| 2 | Bis(9-aza-3-ethyl-8,8,10,10-tetramethyl-1,5-dioxaspiro-[5,5]-3-undecylmethyl)adipate | 400 | 260 |
| Example No. | | | |
| 45 | [structure] | 680 | 620 |
| 46 | [structure] | 660 | 610 |
| 47 | [structure] | 630 | 570 |

TABLE VI-continued

| | Stabilizer | Hours to failure Extruded 1 time | Hours to failure Extruded 5 times |
|---|---|---|---|
| 48 | [complex structure with two 9-aza-3-ethyl-8,8,10,10-tetramethyl-1,5-dioxaspiro[5,5]undecyl groups linked via CH₂OOC(CH₂)₅–[CHCH₂–]–(CH₂)₅COOCH₂ with a branched COOCH₂-dioxaspiro-NH side group] | 650 | 580 |
| 49 | [structure: HN-piperidyl–OOC(CH₂)₅–[CH(Ph)–CH₂]₂–(CH₂)₅COO–piperidyl-NH] | 600 | 520 |
| 50 | [structure: HN-dioxaspiro–CH₂OOC(CH₂)₅–[CHCH₂(Ph)]₂–(CH₂)₅COOCH₂–dioxaspiro-NH] | 590 | 500 |

It is apparent that the stabilizers retained substantially full effectiveness after five extrusions, in contrast to the controls, whose effectiveness diminished by about 40%.

EXAMPLES 51 TO 57

Polyurethane resin compositions were prepared, using stabilizers of the invention and of the prior art, and having the following formulation:

| Ingredient | Parts by Weight |
|---|---|
| Polyurethane resin(Asahi Denka U-100)[1] | 100 |
| Ba stearate | 0.7 |
| Zn stearate | 0.3 |
| 2,6-di-t-butyl-p-cresol | 0.1 |
| Stabilizer as shown in Table VII | 0.3 |

[1] A polyurethane-isocyanurate made from toluene diisocyanate and alkylene polyol.

The stabilizer was blended with the finely-powdered polyurethane resin on a two-roll mill for five minutes at 70° C., and the sheet was then compression molded at 120° C. for five minutes to form sheets 0.5 mm thick. Pieces 2.5 cm square were cut out from the sheets, and exposed to ultraviolet light in a Weather-O-Meter for thirty hours. Elongation before and after exposure was determined, and the percent elongation retained after the exposure is given in Table VII.

TABLE VII

| | Stabilizer | % Retention of elongation |
|---|---|---|
| Control | | |
| 1 | Bis(2,2,6,6-tetramethyl-4-piperidyl) sebacate | 60 |
| 2 | Bis(9-aza-3-ethyl-8,8,10,10-tetramethyl-1,5-dioxaspiro-[5,5]-3-undecylmethyl) adipate | 58 |
| Example No. | | |

TABLE VII-continued
| | Stabilizer | % Retention of elongation |
|---|---|---|
| 51 | 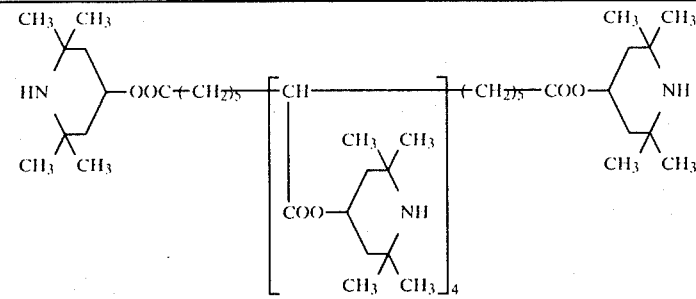 | 79 |
| 52 | 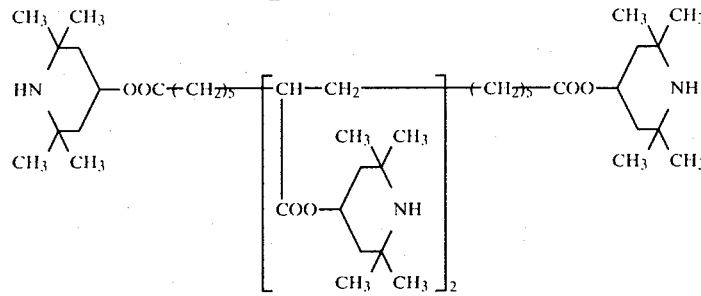 | 77 |
| 53 | 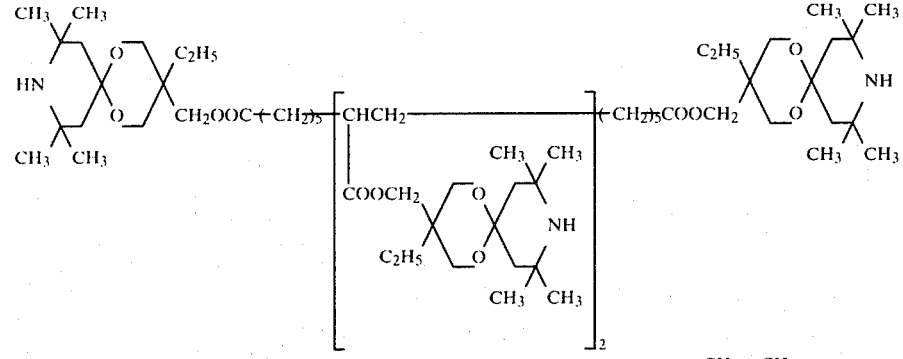 | 76 |
| 54 | 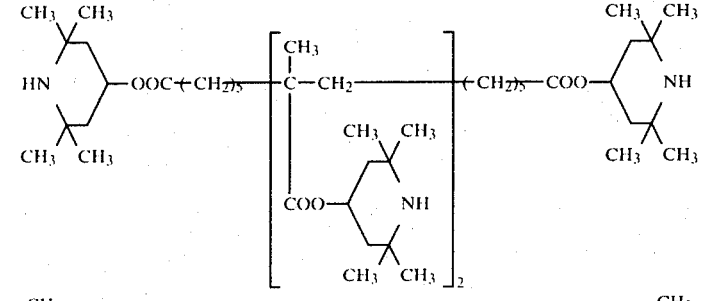 | 76 |
| 55 | 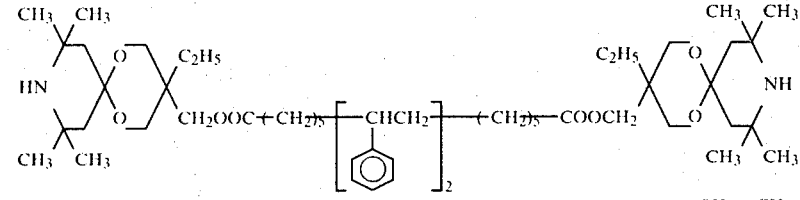 | 74 |
| 56 | 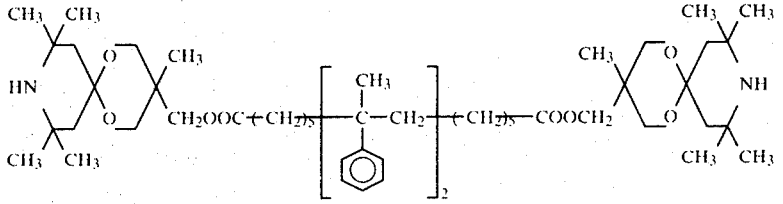 | 74 |

TABLE VII-continued

| | Stabilizer | % Retention of elongation |
|---|---|---|
| 57 | 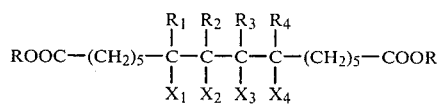 (structure) | 75 |

The stabilizers of the invention are far superior to the controls.

The stabilizers of the invention have also been found to be effective ultraviolet light stabilizers for polycarbonates, polyester resins such as polyethylene terephthalate, polyphenylene, and polyamides such as polycaprolactam.

Having regard to the foregoing disclosure, the following is claimed as the inventive and patentable embodiments thereof:

1. 2,2,6,6-Tetraalkyl-4-piperidyl alcohol esters of tetradecylene polycarboxylic acids having the general formula:

$$ROOC-(CH_2)_5-\overset{\overset{R_1}{|}}{\underset{\underset{X_1}{|}}{C}}-\overset{\overset{R_2}{|}}{\underset{\underset{X_2}{|}}{C}}-\overset{\overset{R_3}{|}}{\underset{\underset{X_3}{|}}{C}}-\overset{\overset{R_4}{|}}{\underset{\underset{X_4}{|}}{C}}-(CH_2)_5-COOR$$

in which:

R is selected from the group consisting of

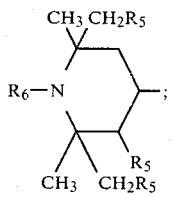

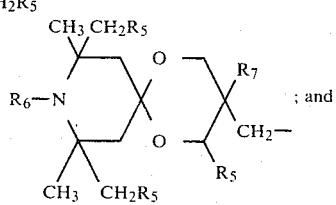; and

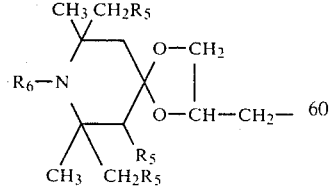

wherein:

$R_5$ and $R_6$ are selected from the group consisting of hydrogen and lower alkyl and hydroxyalkyl having from one to about six carbon atoms;

$R_7$ is lower alkyl having from one to about six carbon atoms;

$R_1$, $R_2$, $R_3$ and $R_4$ are selected from the group consisting of hydrogen and methyl;

$X_1$ and $X_3$ are selected from the group consisting of hydrogen and COOR;

$X_2$ and $X_4$ are selected from the group consisting of COOR and

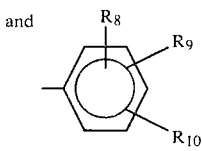

wherein:

$R_8$, $R_9$ and $R_{10}$ are selected from the group consisting of hydrogen, hydroxy, alkyl, and alkoxy having from one to about eighteen carbon atoms.

2. A compound according to claim 1 in which the R is

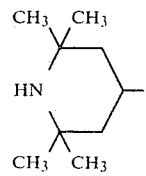

3. A compound according to claim 1 in which the R is

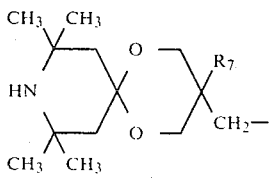

4. A compound according to claim 1 in which the R is

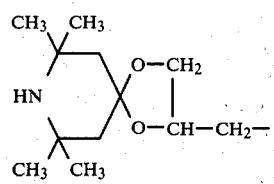

5. A compound according to claim 1 in which $X_1$, $X_2$, $X_3$ and $X_4$ are each COOR.

6. A compound according to claim 5 in which R is

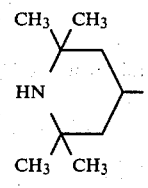

7. A compound according to claim 5 in which R is

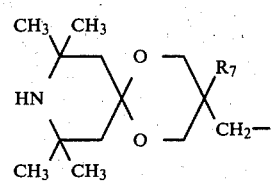

8. A compound according to claim 5 in which R is

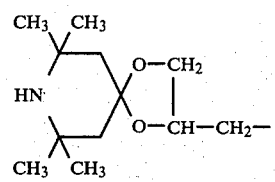

9. A compound according to claim 1 in which $X_1$ and $X_3$ are each hydrogen and $X_2$ and $X_4$ are each phenyl.

10. A compound according to claim 1 in which $X_1$ and $X_3$ are each hydrogen and $X_2$ and $X_4$ are each

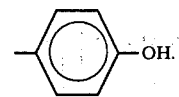

11. A compound according to claim 1 in which $X_1$ and $X_3$ are each hydrogen and $X_2$ and $X_4$ are each

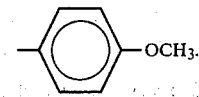

12. A compound according to claim 1 in which $X_1$ and $X_3$ are each hydrogen and $X_2$ and $X_4$ are each

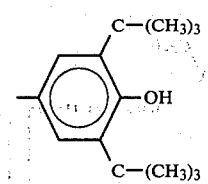

13. A compound according to claim 1 in which $X_1$ and $X_3$ are each hydrogen and $X_2$ and $X_4$ are each 14. A compound according to claim 1 having the formula:

15. A compound according to claim 1 having the formula:

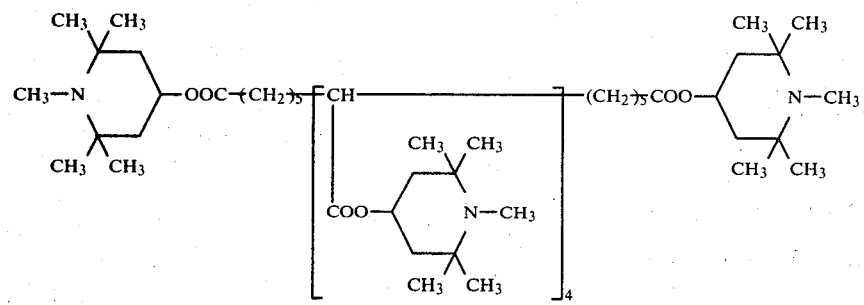
16. A compound according to claim 1 having the formula:
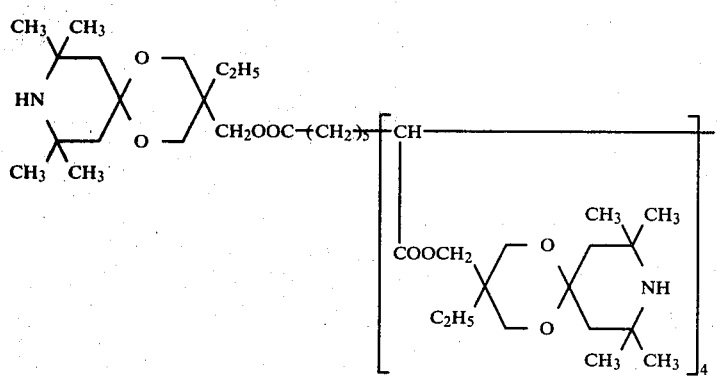
17. A compound according to claim 1 having the formula:
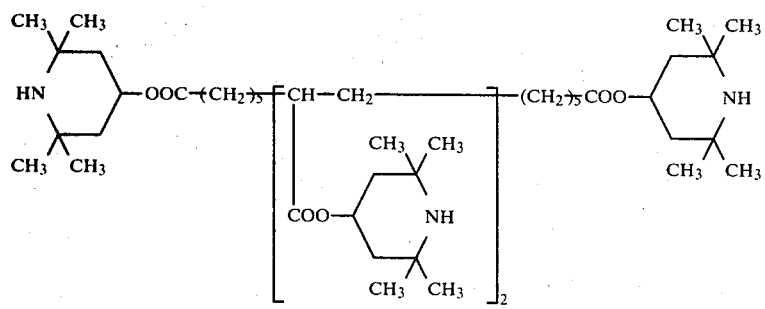
18. A compound according to claim 1 having the formula:
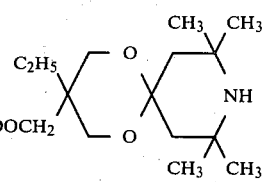
19. A compound according to claim 1 having the formula:
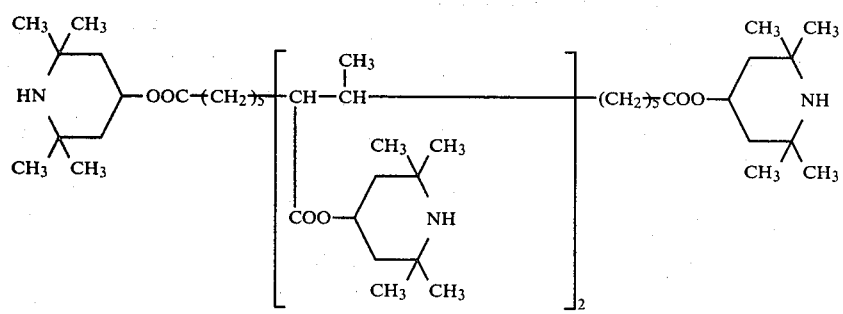

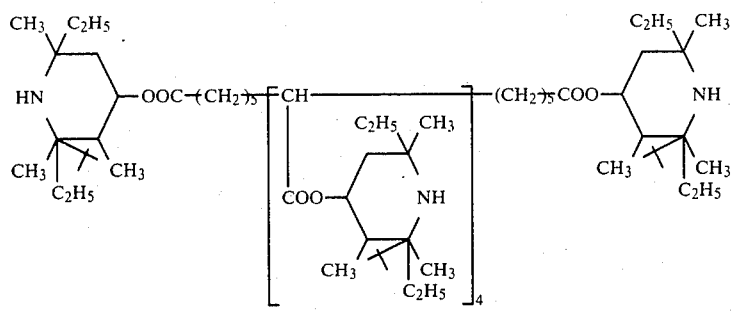

20. A polyvinyl chloride resin composition having improved resistance to deterioration when heated at 350° F., comprising a polyvinyl chloride resin formed at least in part of the recurring group:

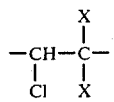

and having a chlorine content in excess of 40%, where X is either hydrogen or chlorine; and a compound in accordance with claim 1.

21. A polyvinyl chloride resin composition in accordance with claim 20 in which the polyvinyl chloride resin is polyvinyl chloride homopolymer.

22. A polyvinyl chloride resin composition in accordance with claim 20 in which the polyvinyl chloride resin is a copolymer of vinyl chloride and vinyl acetate.

23. An olefin polymer composition having improved resistance to deterioration comprising an olefin polymer selected from the group consisting of polymers of alpha-olefins having from two to six carbon atoms and polystyrene, and a compound in accordance with claim 1.

24. An olefin polymer composition in accordance with claim 23 wherein the polyolefin is polypropylene.

25. An olefin polymer composition in accordance with claim 23, wherein the polyolefin is polyethylene.

26. An acrylonitrile-butadiene-styrene polymer having its resistance to deterioration when heated at 300° F. and above enhanced by a compound in accordance with claim 1.

27. A polyester resin composition having improved resistance to deterioration comprising a polyester resin and a compound in accordance with claim 1.

28. An ethylene-vinyl acetate copolymer composition having improved resistance to deterioration comprising an ethylene-vinyl acetate copolymer and a compound in accordance with claim 1.

* * * * *

UNITED STATES PATENT AND TRADEMARK OFFICE
CERTIFICATE OF CORRECTION

PATENT NO. : 4,312,804
DATED : January 26, 1982
INVENTOR(S) : Motonobu Minagawa et al It is certified that error appears in the above-identified patent and that said Letters Patent are hereby corrected as shown below:

Cover page, in the Abstract,
line 42 : before "wherein" delete "30"
Column 2, lines 10 to 16 : " 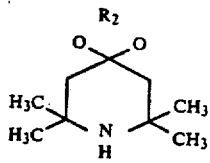 " should be -- 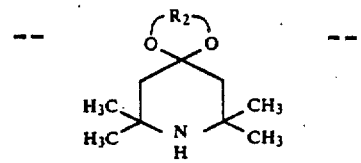 --

| | | |
|---|---|---|
| Column 6, line 50 | : | "0-" should be -- O-  -- |
| Column 8, line 60 | : | "cyclalkyl" should be --cycloalkyl-- |
| Column 10, line 25 | : | after "residue" insert --having-- |
| Column 10, line 52 | : | "$-R_8$)" should be -- $\{R_8\}$ -- |
| Column 12, line 33 | : | "significanace" should be --significances-- |
| Column 14, line 31 | : | after "$R^e$" insert --and-- |
| Column 14, line 34 | : | "either" should be --neither-- |
| Column 15, line 21 | : | "alkylene" should be --alkenylene-- |
| Column 16, line 23 | : | "O" should be —O˙-- |
| Column 16, line 40 | : | "alchol" should be -- alcohol-- |
| Column 17, line 18 | : | "$X_2$" should be --$X_3$-- |
| Column 17, line 31 | : | "$R_8$;" should be --$R_8$, -- |

UNITED STATES PATENT AND TRADEMARK OFFICE
CERTIFICATE OF CORRECTION

PATENT NO. : 4,312,804
DATED : January 26, 1982
INVENTOR(S) : Motonobu Minagawa et al It is certified that error appears in the above-identified patent and that said Letters Patent are hereby corrected as shown below:

Column 23, lines 26 to 33 : "

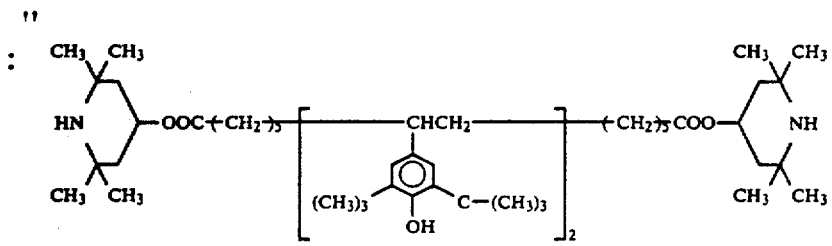

should be

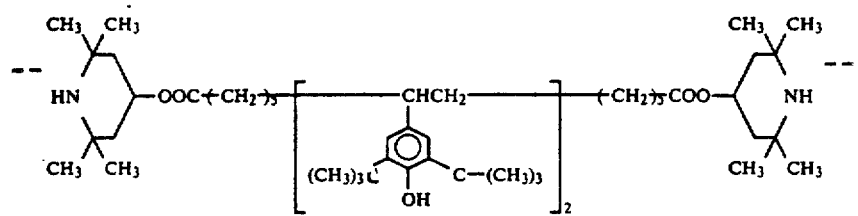

Column 25, line 61 : "piperidinyl" should be --piperidyl--

Column 27, lines 1 to 15 : "

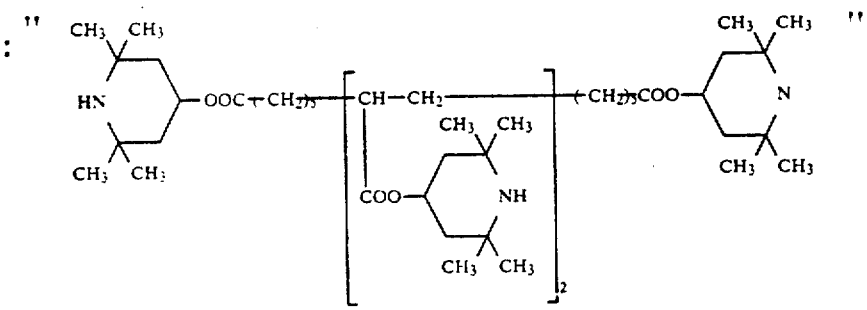

"

UNITED STATES PATENT AND TRADEMARK OFFICE
CERTIFICATE OF CORRECTION

PATENT NO. : 4,312,804
DATED : January 26, 1982
INVENTOR(S) : Motonobu Minagawa et al It is certified that error appears in the above-identified patent and that said Letters Patent are hereby corrected as shown below:

should be

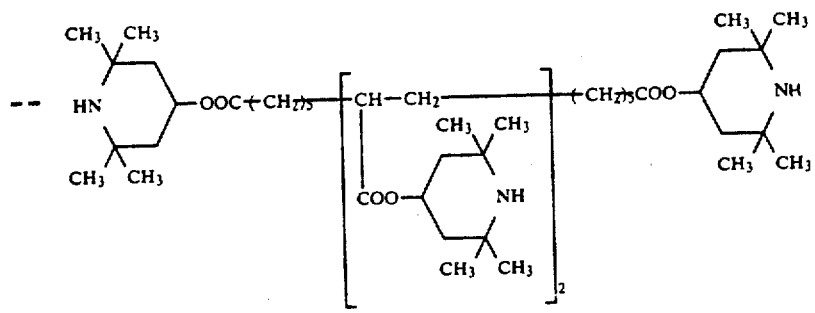

Column 28, line 60 : after "these" insert --sheets--

Column 29, lines 37 to 45 : "

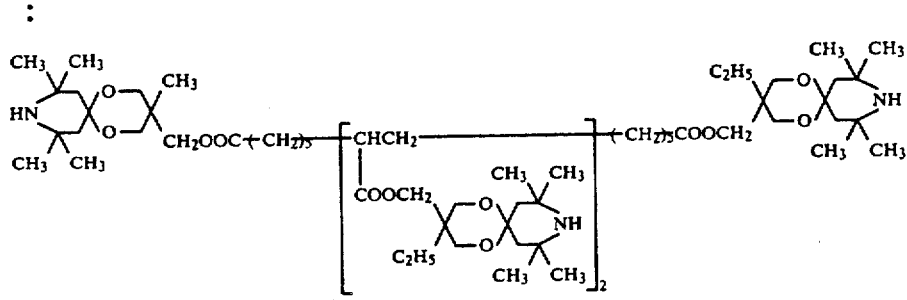

should be

UNITED STATES PATENT AND TRADEMARK OFFICE
CERTIFICATE OF CORRECTION

PATENT NO. : 4,312,804
DATED : January 26, 1982
INVENTOR(S) : Motonobu Minagawa et al It is certified that error appears in the above—identified patent and that said Letters Patent is hereby corrected as shown below:

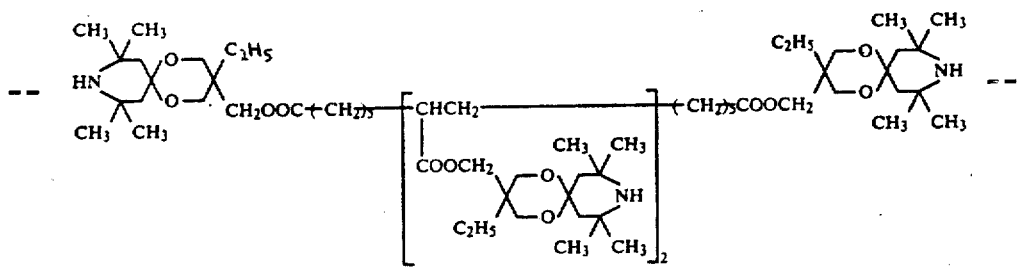

Column 35, before the first line insert --EXAMPLES 19 TO 25 --

Column 37, lines 5 to 12 "

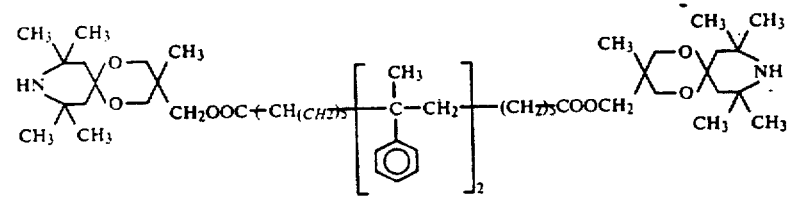

should be

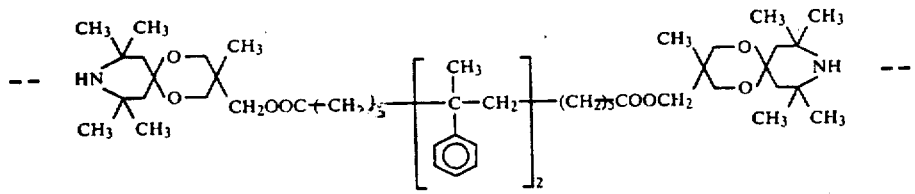

UNITED STATES PATENT AND TRADEMARK OFFICE
CERTIFICATE OF CORRECTION

PATENT NO. : 4,312,804

DATED : January 26, 1982

INVENTOR(S) : Motonobu Minagawa et al

Page 5 of 5

It is certified that error appears in the above-identified patent and that said Letters Patent is hereby corrected as shown below:

Column 57, lines 1 to 13 : " 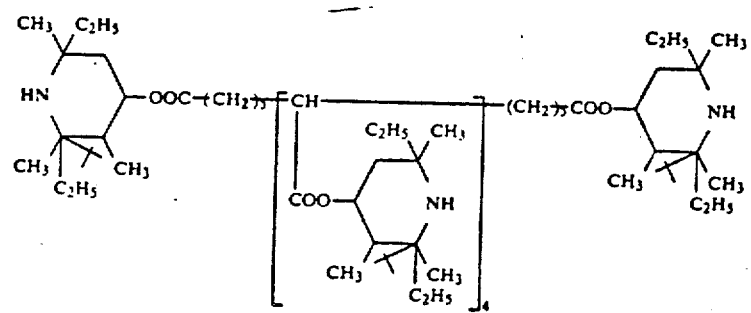 "

should be 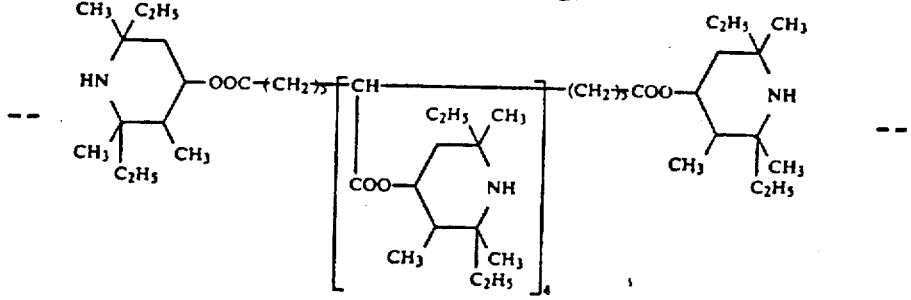

Signed and Sealed this

Twentieth Day of October, 1987

Attest:

DONALD J. QUIGG

Attesting Officer

Commissioner of Patents and Trademarks